United States Patent
Sierra et al.

(10) Patent No.: US 11,712,299 B2
(45) Date of Patent: *Aug. 1, 2023

(54) PICOSECOND LASER APPARATUS AND METHODS FOR ITS OPERATION AND USE

(71) Applicant: Cynosure, LLC., Westford, MA (US)

(72) Inventors: Rafael Armando Sierra, Palmer, MA (US); Mirko Mirkov, Chelmsford, MA (US); Richard Shaun Welches, Manchester, NH (US)

(73) Assignee: Cynosure, LLC., Westford, MA (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/221,869

(22) Filed: Apr. 5, 2021

(65) Prior Publication Data

US 2021/0244470 A1 Aug. 12, 2021

Related U.S. Application Data

(60) Continuation of application No. 17/070,119, filed on Oct. 14, 2020, now Pat. No. 10,966,785, which is a
(Continued)

(51) Int. Cl.
*A61B 18/20* (2006.01)
*H01S 3/00* (2006.01)
(Continued)

(52) U.S. Cl.
CPC .......... *A61B 18/203* (2013.01); *A61N 5/0616* (2013.01); *H01S 3/00* (2013.01);
(Continued)

(58) Field of Classification Search
CPC ........ A61B 18/203; A61B 2017/00769; A61B 2018/00452; A61B 2018/0047;
(Continued)

(56) References Cited

U.S. PATENT DOCUMENTS

| 853,033 A | 5/1907 | Roberts |
| 1,590,283 A | 6/1926 | Catlin |

(Continued)

FOREIGN PATENT DOCUMENTS

| AT | 100305 B | 12/1995 |
| AU | 1851583 A | 3/1984 |

(Continued)

OTHER PUBLICATIONS

Ohbayashi, "Stimulatory Effect of Laser Irradiation on Calcified Nodule Formation in Human Dental Pulp Fibroblasts," Abstract J-Endod. Jan. 1999; 25(1): 30-3.
(Continued)

*Primary Examiner* — Aaron F Roane

(74) *Attorney, Agent, or Firm* — Banner & Witcoff, Ltd.

(57) ABSTRACT

Apparatuses and methods are disclosed for applying laser energy having desired pulse characteristics, including a sufficiently short duration and/or a sufficiently high energy for the photomechanical treatment of skin pigmentations and pigmented lesions, both naturally-occurring (e.g., birthmarks), as well as artificial (e.g., tattoos). The laser energy may be generated with an apparatus having a resonator with the capability of switching between a modelocked pulse operating mode and an amplification operating mode. The operating modes are carried out through the application of a time-dependent bias voltage, having waveforms as described herein, to an electro-optical device (e.g., a Pockels cell) positioned along the optical axis of the resonator.

14 Claims, 4 Drawing Sheets

Related U.S. Application Data division of application No. 14/708,828, filed on May 11, 2015, now Pat. No. 10,849,687, which is a continuation of application No. 12/534,379, filed on Aug. 3, 2009, now Pat. No. 9,028,536, which is a division of application No. 11/461,812, filed on Aug. 2, 2006, now Pat. No. 7,586,957.

(51) Int. Cl.
| | |
|---|---|
| *A61N 5/06* | (2006.01) |
| *A61B 17/00* | (2006.01) |
| *A61B 18/00* | (2006.01) |
| *G02F 1/03* | (2006.01) |
| *H01S 3/11* | (2023.01) |
| *H01S 3/1109* | (2023.01) |
| *H01S 3/115* | (2006.01) |
| *A61N 5/067* | (2006.01) |
| *H01S 3/107* | (2006.01) |

(52) U.S. Cl.
CPC .............. *A61B 2017/00769* (2013.01); *A61B 2018/0047* (2013.01); *A61B 2018/00452* (2013.01); *A61N 5/067* (2021.08); *G02F 1/0327* (2013.01); *H01S 3/107* (2013.01); *H01S 3/1103* (2013.01); *H01S 3/115* (2013.01); *H01S 3/1109* (2013.01)

(58) Field of Classification Search
CPC ........ A61N 5/0616; A61N 5/067; H01S 3/00; H01S 3/107; H01S 3/1103; H01S 3/1109; H01S 3/115; G02F 1/0327
USPC .......................................................... 607/89
See application file for complete search history.

(56) References Cited

U.S. PATENT DOCUMENTS

| | | |
|---|---|---|
| 1,676,183 A | 7/1928 | Garfunkle |
| 1,706,161 A | 3/1929 | Hollnagel |
| 2,068,721 A | 1/1937 | Wappler et al. |
| 2,472,385 A | 6/1949 | Rollman |
| 2,669,771 A | 2/1954 | Burge et al. |
| 3,243,650 A | 3/1966 | Hawkins et al. |
| 3,261,978 A | 7/1966 | Brenman |
| 3,284,665 A | 11/1966 | Goncz |
| 3,327,712 A | 6/1967 | Kaufman et al. |
| 3,465,203 A | 9/1969 | Galster et al. |
| 3,486,070 A | 12/1969 | Engel |
| 3,524,144 A | 8/1970 | Buser et al. |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,651,425 A | 3/1972 | McKnight |
| 3,653,778 A | 4/1972 | Freiling |
| 3,667,454 A | 6/1972 | Prince |
| 3,693,623 A | 9/1972 | Harte et al. |
| 3,699,967 A | 10/1972 | Anderson |
| 3,725,733 A | 4/1973 | Mack et al. |
| 3,766,393 A | 10/1973 | Herzog et al. |
| 3,766,488 A | 10/1973 | Kohn |
| 3,769,963 A | 11/1973 | Goldman et al. |
| 3,793,723 A | 2/1974 | Kuris et al. |
| 3,794,028 A | 2/1974 | Mueller et al. |
| 3,815,046 A | 6/1974 | Johnson et al. |
| 3,818,373 A | 6/1974 | Chun et al. |
| 3,818,914 A | 6/1974 | Bender |
| 3,821,510 A | 6/1974 | Muncheryan |
| 3,834,391 A | 9/1974 | Block |
| 3,843,865 A | 10/1974 | Nath |
| 3,846,811 A | 11/1974 | Nakamura et al. |
| 3,857,015 A | 12/1974 | Clark et al. |
| 3,858,577 A | 1/1975 | Bass et al. |
| 3,861,921 A | 1/1975 | Hoffmann et al. |
| 3,885,569 A | 5/1975 | Judson |
| 3,890,537 A | 6/1975 | Park et al. |
| 3,900,034 A | 8/1975 | Katz et al. |
| 3,909,649 A | 9/1975 | Arsena |
| 3,914,709 A | 10/1975 | Pike et al. |
| 3,939,560 A | 2/1976 | Lyall |
| 3,977,083 A | 8/1976 | Leslie et al. |
| 3,980,861 A | 9/1976 | Fukunaga |
| 4,019,156 A | 4/1977 | Fountain et al. |
| 4,037,136 A | 7/1977 | Hoene |
| 4,038,984 A | 8/1977 | Sittner |
| 4,047,106 A | 9/1977 | Robinson |
| 4,065,370 A | 12/1977 | Noble et al. |
| 4,122,853 A | 10/1978 | Smith |
| 4,133,503 A | 1/1979 | Bliss |
| 4,139,342 A | 2/1979 | Sheldrake et al. |
| 4,154,240 A | 5/1979 | Ikuno et al. |
| 4,176,324 A | 11/1979 | Aldag et al. |
| 4,176,327 A | 11/1979 | Wayne et al. |
| 4,188,927 A | 2/1980 | Harris |
| 4,213,462 A | 7/1980 | Sato |
| 4,228,800 A | 10/1980 | Degler, Jr. et al. |
| 4,233,493 A | 11/1980 | Nath |
| 4,254,333 A | 3/1981 | Bergstrom |
| 4,259,123 A | 3/1981 | Tymkewicz |
| 4,269,067 A | 5/1981 | Tynan et al. |
| 4,273,109 A | 6/1981 | Enderby |
| 4,275,335 A | 6/1981 | Ishida |
| 4,291,281 A | 9/1981 | Pinard et al. |
| 4,292,601 A | 9/1981 | Aldag et al. |
| 4,293,827 A | 10/1981 | McAllister et al. |
| 4,298,005 A | 11/1981 | Mutzhas |
| 4,299,912 A | 11/1981 | Shiba et al. |
| 4,302,730 A | 11/1981 | Jernigan |
| 4,313,431 A | 2/1982 | Frank |
| 4,316,467 A | 2/1982 | Muckerheide |
| 4,333,197 A | 6/1982 | Kuris |
| 4,335,726 A | 6/1982 | Kolstedt |
| 4,336,809 A | 6/1982 | Clark |
| 4,364,015 A | 12/1982 | Drake et al. |
| 4,375,684 A | 3/1983 | Everett |
| 4,388,924 A | 6/1983 | Weissman et al. |
| 4,409,479 A | 10/1983 | Sprague et al. |
| 4,428,368 A | 1/1984 | Torii |
| 4,435,808 A | 3/1984 | Javan |
| 4,445,217 A | 4/1984 | Acharekar et al. |
| 4,452,081 A | 6/1984 | Seppi |
| 4,456,872 A | 6/1984 | Froeschle |
| 4,461,294 A | 7/1984 | Baron |
| 4,488,104 A | 12/1984 | Suzuki |
| 4,489,415 A | 12/1984 | Jones, Jr. |
| 4,492,601 A | 1/1985 | Nakasone et al. |
| 4,503,854 A | 3/1985 | Jako |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,555,786 A | 11/1985 | Byer |
| 4,556,979 A | 12/1985 | Scott et al. |
| 4,559,943 A | 12/1985 | Bowers |
| 4,561,440 A | 12/1985 | Kubo et al. |
| 4,566,271 A | 1/1986 | French et al. |
| 4,566,438 A | 1/1986 | Liese et al. |
| 4,569,345 A | 2/1986 | Manes |
| 4,576,177 A | 3/1986 | Webster, Jr. |
| 4,587,968 A | 5/1986 | Price |
| 4,591,762 A | 5/1986 | Nakamura |
| 4,592,353 A | 6/1986 | Daikuzono |
| 4,601,037 A | 7/1986 | McDonald |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,638,800 A | 1/1987 | Michel |
| 4,653,495 A | 3/1987 | Nanaumi |

(56) References Cited

U.S. PATENT DOCUMENTS

| | | |
|---|---|---|
| 4,656,641 A | 4/1987 | Scifres et al. |
| 4,662,368 A | 5/1987 | Hussein et al. |
| 4,677,347 A | 6/1987 | Nakamura |
| 4,686,986 A | 8/1987 | Fenyo et al. |
| 4,693,244 A | 9/1987 | Daikuzono |
| 4,693,556 A | 9/1987 | McCaughan, Jr. |
| 4,695,697 A | 9/1987 | Kosa |
| 4,710,677 A | 12/1987 | Halberstadt et al. |
| 4,718,416 A | 1/1988 | Nanaumi |
| 4,724,835 A | 2/1988 | Liss et al. |
| 4,733,660 A | 3/1988 | Itzkan |
| 4,735,201 A | 4/1988 | O'Reilly |
| 4,736,743 A | 4/1988 | Daikuzono |
| 4,736,745 A | 4/1988 | Gluckman |
| 4,740,047 A | 4/1988 | Abe et al. |
| 4,741,338 A | 5/1988 | Miyamae |
| 4,745,909 A | 5/1988 | Pelton et al. |
| 4,747,660 A | 5/1988 | Nishioka et al. |
| 4,749,913 A | 6/1988 | Stuermer et al. |
| 4,759,349 A | 7/1988 | Betz et al. |
| 4,773,413 A | 9/1988 | Hussein et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,813,412 A | 3/1989 | Yamazaki et al. |
| 4,813,762 A | 3/1989 | Leger et al. |
| 4,819,669 A | 4/1989 | Politzer |
| 4,826,431 A | 5/1989 | Fujimura et al. |
| 4,829,262 A | 5/1989 | Furumoto |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,848,339 A | 7/1989 | Rink et al. |
| 4,852,107 A | 7/1989 | Hamal et al. |
| 4,852,549 A | 8/1989 | Mori |
| 4,860,172 A | 8/1989 | Schlager et al. |
| 4,860,303 A | 8/1989 | Russell |
| 4,860,743 A | 8/1989 | Abela |
| 4,860,744 A | 8/1989 | Johnson et al. |
| 4,862,886 A | 9/1989 | Clarke et al. |
| 4,862,888 A | 9/1989 | Yessik |
| 4,862,903 A | 9/1989 | Campbell |
| 4,871,479 A | 10/1989 | Bachelard et al. |
| 4,878,224 A | 10/1989 | Kuder et al. |
| 4,884,560 A | 12/1989 | Kuracina |
| 4,887,600 A | 12/1989 | Watson et al. |
| 4,889,525 A | 12/1989 | Yuhas et al. |
| 4,890,898 A | 1/1990 | Bentley et al. |
| 4,891,817 A | 1/1990 | Duarte |
| 4,896,329 A | 1/1990 | Knaak |
| 4,898,438 A | 2/1990 | Mori |
| 4,898,439 A | 2/1990 | Mori |
| 4,901,323 A | 2/1990 | Hawkins et al. |
| 4,905,690 A | 3/1990 | Ohshiro et al. |
| 4,910,438 A | 3/1990 | Farnsworth |
| 4,913,142 A | 4/1990 | Kittrell et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,931,053 A | 6/1990 | L'Esperance, Jr. |
| 4,932,954 A | 6/1990 | Wondrazek et al. |
| 4,945,239 A | 7/1990 | Wist et al. |
| 4,950,266 A | 8/1990 | Sinofsky |
| 4,955,882 A | 9/1990 | Hakky |
| 4,968,314 A | 11/1990 | Michaels |
| 4,972,427 A | 11/1990 | Streifer et al. |
| 4,973,848 A | 11/1990 | Kolobanov et al. |
| 4,976,308 A | 12/1990 | Faghri |
| 4,976,709 A | 12/1990 | Sand |
| 4,977,571 A | 12/1990 | Furumoto et al. |
| 4,978,186 A | 12/1990 | Mori |
| 4,979,180 A | 12/1990 | Muncheryan |
| 4,992,256 A | 2/1991 | Skaggs et al. |
| 4,994,060 A | 2/1991 | Rink et al. |
| 5,000,752 A | 3/1991 | Hoskin et al. |
| 5,006,293 A | 4/1991 | Hartman et al. |
| 5,009,658 A | 4/1991 | Damgaard-Iversen et al. |
| 5,011,483 A | 4/1991 | Sleister |
| 5,027,359 A | 6/1991 | Leger et al. |
| 5,030,090 A | 7/1991 | Maeda et al. |
| 5,032,178 A | 7/1991 | Cornell |
| 5,037,421 A | 8/1991 | Boutacoff et al. |
| 5,041,109 A | 8/1991 | Abela |
| 5,046,494 A | 9/1991 | Searfoss et al. |
| 5,050,597 A | 9/1991 | Daikuzono |
| 5,056,515 A | 10/1991 | Abel |
| 5,057,099 A | 10/1991 | Rink |
| 5,057,104 A | 10/1991 | Chess |
| 5,059,192 A | 10/1991 | Zaias |
| 5,060,243 A | 10/1991 | Eckert |
| 5,061,266 A | 10/1991 | Hakky |
| 5,065,515 A | 11/1991 | Iderosa |
| 5,066,292 A | 11/1991 | Muller et al. |
| 5,066,293 A | 11/1991 | Furumoto |
| 5,071,416 A | 12/1991 | Heller et al. |
| 5,071,417 A | 12/1991 | Sinofsky |
| 5,080,660 A | 1/1992 | Buelna |
| 5,090,019 A | 2/1992 | Scheps |
| 5,092,865 A | 3/1992 | Rink |
| 5,099,231 A | 3/1992 | Sato et al. |
| 5,102,410 A | 4/1992 | Dressel |
| 5,108,388 A | 4/1992 | Trokel |
| 5,109,387 A | 4/1992 | Garden et al. |
| 5,112,328 A | 5/1992 | Taboada et al. |
| 5,127,395 A | 7/1992 | Bontemps |
| 5,129,896 A | 7/1992 | Hasson |
| 5,129,897 A | 7/1992 | Daikuzono |
| 5,132,980 A | 7/1992 | Connors et al. |
| 5,133,102 A | 7/1992 | Sakuma |
| 5,137,530 A | 8/1992 | Sand |
| 5,140,608 A | 8/1992 | Karpol et al. |
| 5,140,984 A | 8/1992 | Dew et al. |
| 5,147,353 A | 9/1992 | Everett |
| 5,147,356 A | 9/1992 | Bhatta |
| 5,151,097 A | 9/1992 | Daikuzono |
| 5,159,601 A | 10/1992 | Huber |
| 5,160,194 A | 11/1992 | Feldman |
| 5,163,935 A | 11/1992 | Black et al. |
| 5,171,564 A | 12/1992 | Nathoo et al. |
| 5,178,617 A | 1/1993 | Kuizenga et al. |
| 5,180,378 A | 1/1993 | Kung et al. |
| 5,182,557 A | 1/1993 | Lang |
| 5,182,857 A | 2/1993 | Simon |
| 5,190,541 A | 3/1993 | Abele et al. |
| 5,191,883 A | 3/1993 | Lennox et al. |
| 5,192,278 A | 3/1993 | Hayes et al. |
| 5,193,526 A | 3/1993 | Daikuzono |
| 5,196,004 A | 3/1993 | Sinofsky |
| 5,197,470 A | 3/1993 | Helfer et al. |
| 5,201,731 A | 4/1993 | Hakky |
| 5,207,671 A | 5/1993 | Franken et al. |
| 5,207,672 A | 5/1993 | Roth et al. |
| 5,207,673 A | 5/1993 | Ebling et al. |
| 5,209,748 A | 5/1993 | Daikuzono |
| 5,213,092 A | 5/1993 | Uram |
| 5,217,455 A | 6/1993 | Tan |
| 5,219,347 A | 6/1993 | Negus et al. |
| 5,222,907 A | 6/1993 | Katabuchi et al. |
| 5,222,953 A | 6/1993 | Dowlatshahi |
| 5,225,926 A | 7/1993 | Cuomo et al. |
| 5,226,907 A | 7/1993 | Tankovich |
| 5,242,437 A | 9/1993 | Everett et al. |
| 5,242,438 A | 9/1993 | Saadatmanesh et al. |
| 5,246,436 A | 9/1993 | Rowe |
| 5,249,192 A | 9/1993 | Kuizenga et al. |
| 5,254,114 A | 10/1993 | Reed, Jr. et al. |
| 5,255,277 A | 10/1993 | Carvalho |
| 5,257,970 A | 11/1993 | Dougherty |
| 5,257,991 A | 11/1993 | Fletcher et al. |
| 5,261,904 A | 11/1993 | Baker et al. |

(56) References Cited

U.S. PATENT DOCUMENTS

| | | |
|---|---|---|
| 5,267,399 A | 12/1993 | Johnston |
| 5,267,995 A | 12/1993 | Doiron et al. |
| 5,267,998 A | 12/1993 | Hagen |
| 5,269,777 A | 12/1993 | Doiron et al. |
| 5,269,780 A | 12/1993 | Roos |
| 5,281,211 A | 1/1994 | Parel et al. |
| 5,281,216 A | 1/1994 | Klicek |
| 5,282,797 A | 2/1994 | Chess |
| 5,284,154 A | 2/1994 | Raymond et al. |
| 5,287,372 A | 2/1994 | Ortiz |
| 5,287,380 A | 2/1994 | Hsia |
| 5,290,273 A | 3/1994 | Tan |
| 5,290,274 A | 3/1994 | Levy et al. |
| 5,292,320 A | 3/1994 | Brown et al. |
| 5,293,880 A | 3/1994 | Levitt |
| 5,300,063 A | 4/1994 | Tano et al. |
| 5,300,065 A | 4/1994 | Anderson |
| 5,300,097 A | 4/1994 | Lerner et al. |
| 5,303,585 A | 4/1994 | Lichte |
| 5,304,167 A | 4/1994 | Freiberg |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,307,369 A | 4/1994 | Kimberlin |
| 5,308,311 A | 5/1994 | Eggers et al. |
| 5,312,395 A | 5/1994 | Tan et al. |
| 5,312,396 A | 5/1994 | Feld et al. |
| 5,320,618 A | 6/1994 | Gustafsson |
| 5,320,620 A | 6/1994 | Long et al. |
| 5,330,470 A | 7/1994 | Hagen |
| 5,331,649 A | 7/1994 | Dacquay et al. |
| 5,334,191 A | 8/1994 | Poppas et al. |
| 5,334,193 A | 8/1994 | Nardella |
| 5,336,217 A | 8/1994 | Buys et al. |
| 5,336,221 A | 8/1994 | Anderson |
| 5,342,358 A | 8/1994 | Daikuzono |
| 5,344,418 A | 9/1994 | Ghaffari |
| 5,344,434 A | 9/1994 | Talmore |
| 5,346,488 A | 9/1994 | Prince et al. |
| 5,348,551 A | 9/1994 | Spears et al. |
| 5,349,590 A | 9/1994 | Amirkhanian et al. |
| 5,350,376 A | 9/1994 | Brown |
| 5,353,020 A | 10/1994 | Schumann |
| 5,353,790 A | 10/1994 | Jacques et al. |
| 5,354,294 A | 10/1994 | Chou |
| 5,356,081 A | 10/1994 | Sellar |
| 5,358,503 A | 10/1994 | Bertwell et al. |
| 5,360,426 A | 11/1994 | Muller et al. |
| 5,366,456 A | 11/1994 | Rink et al. |
| 5,368,031 A | 11/1994 | Cline et al. |
| 5,368,038 A | 11/1994 | Fraden |
| 5,369,496 A | 11/1994 | Alfano et al. |
| 5,369,831 A | 12/1994 | Bock |
| 5,370,642 A | 12/1994 | Keller |
| 5,370,649 A | 12/1994 | Gardetto et al. |
| 5,380,317 A | 1/1995 | Everett et al. |
| 5,383,876 A | 1/1995 | Nardella |
| 5,386,427 A | 1/1995 | Zayhowski |
| 5,387,211 A | 2/1995 | Saadatmanesh et al. |
| 5,395,356 A | 3/1995 | King et al. |
| 5,403,306 A | 4/1995 | Edwards et al. |
| 5,405,368 A | 4/1995 | Eckhouse |
| 5,409,446 A | 4/1995 | Rattner |
| 5,409,479 A | 4/1995 | Dew et al. |
| 5,409,481 A | 4/1995 | Poppas et al. |
| 5,415,654 A | 5/1995 | Daikuzono |
| 5,421,337 A | 6/1995 | Richards-Kortum et al. |
| 5,421,339 A | 6/1995 | Ramanujam et al. |
| 5,422,112 A | 6/1995 | Williams |
| 5,423,800 A | 6/1995 | Ren et al. |
| 5,423,803 A | 6/1995 | Tankovich et al. |
| 5,423,805 A | 6/1995 | Brucker et al. |
| 5,425,728 A | 6/1995 | Tankovich |
| 5,425,735 A | 6/1995 | Rosen et al. |
| 5,425,754 A | 6/1995 | Braun et al. |
| 5,439,954 A | 8/1995 | Bush |
| 5,441,499 A | 8/1995 | Fritzsch |
| 5,445,608 A | 8/1995 | Chen et al. |
| 5,445,611 A | 8/1995 | Eppstein et al. |
| 5,454,807 A | 10/1995 | Lennox et al. |
| 5,456,682 A | 10/1995 | Edwards et al. |
| 5,458,140 A | 10/1995 | Eppstein et al. |
| 5,464,436 A | 11/1995 | Smith |
| 5,464,724 A | 11/1995 | Akiyama et al. |
| 5,470,331 A | 11/1995 | Daikuzono |
| 5,472,748 A | 12/1995 | Wolfe et al. |
| 5,474,549 A | 12/1995 | Ortiz et al. |
| 5,484,436 A | 1/1996 | Eggers et al. |
| 5,486,170 A | 1/1996 | Winston et al. |
| 5,486,172 A | 1/1996 | Chess |
| 5,488,626 A | 1/1996 | Heller et al. |
| 5,489,256 A | 2/1996 | Adair |
| 5,492,894 A | 2/1996 | Bascom et al. |
| 5,496,305 A | 3/1996 | Kittrell et al. |
| 5,496,307 A | 3/1996 | Daikuzono |
| 5,498,935 A | 3/1996 | McMahan et al. |
| 5,499,313 A | 3/1996 | Kleinerman |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,507,739 A | 4/1996 | Vassiliadis et al. |
| 5,519,534 A | 5/1996 | Smith et al. |
| 5,521,367 A | 5/1996 | Bard et al. |
| 5,522,813 A | 6/1996 | Trelles |
| 5,527,350 A | 6/1996 | Grove et al. |
| 5,527,368 A | 6/1996 | Supkis et al. |
| 5,530,711 A | 6/1996 | Scheps |
| 5,531,739 A | 7/1996 | Trelles |
| 5,531,740 A | 7/1996 | Black |
| 5,536,168 A | 7/1996 | Bourke |
| 5,540,676 A | 7/1996 | Freiberg |
| 5,540,678 A | 7/1996 | Long |
| 5,540,681 A | 7/1996 | Strul et al. |
| 5,541,948 A | 7/1996 | Krupke et al. |
| 5,546,214 A | 8/1996 | Black et al. |
| 5,549,660 A | 8/1996 | Mendes et al. |
| 5,557,625 A | 9/1996 | Durville |
| 5,558,666 A | 9/1996 | Dewey et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,029 A | 11/1996 | Trelles et al. |
| 5,578,866 A | 11/1996 | DePoorter et al. |
| 5,595,568 A | 1/1997 | Anderson et al. |
| 5,598,426 A | 1/1997 | Hsia et al. |
| 5,608,210 A | 3/1997 | Esparza et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse |
| 5,624,435 A | 4/1997 | Furumoto et al. |
| 5,626,631 A | 5/1997 | Eckhouse |
| 5,628,744 A | 5/1997 | Coleman et al. |
| 5,628,771 A | 5/1997 | Mizukawa et al. |
| 5,630,811 A | 5/1997 | Miller |
| 5,632,741 A | 5/1997 | Zavislan et al. |
| 5,634,711 A | 6/1997 | Kennedy et al. |
| 5,647,866 A | 7/1997 | Zaias et al. |
| 5,649,972 A | 7/1997 | Hochstein |
| 5,651,783 A | 7/1997 | Reynard |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,668,824 A | 9/1997 | Furumoto et al. |
| 5,671,315 A | 9/1997 | Tabuchi et al. |

(56) References Cited

U.S. PATENT DOCUMENTS

| | | |
|---|---|---|
| 5,673,451 A | 10/1997 | Moore et al. |
| 5,679,113 A | 10/1997 | Caisey et al. |
| 5,683,380 A | 11/1997 | Eckhouse et al. |
| 5,684,902 A | 11/1997 | Tada |
| 5,688,266 A | 11/1997 | Edwards et al. |
| 5,688,267 A | 11/1997 | Panescu et al. |
| 5,692,509 A | 12/1997 | Voss et al. |
| 5,698,866 A | 12/1997 | Doiron et al. |
| 5,707,369 A | 1/1998 | Vaitekunas et al. |
| 5,707,401 A | 1/1998 | Talmore |
| 5,707,403 A | 1/1998 | Grove et al. |
| 5,713,738 A | 2/1998 | Yarborough |
| 5,714,119 A | 2/1998 | Kawagoe et al. |
| 5,720,772 A | 2/1998 | Eckhouse |
| 5,720,894 A | 2/1998 | Neev et al. |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,749,868 A | 5/1998 | Furumoto |
| 5,755,751 A | 5/1998 | Eckhouse |
| 5,759,162 A | 6/1998 | Oppelt et al. |
| 5,759,200 A | 6/1998 | Azar |
| 5,760,362 A | 6/1998 | Eloy |
| 5,769,076 A | 6/1998 | Maekawa et al. |
| 5,776,129 A | 7/1998 | Mersch |
| 5,782,249 A | 7/1998 | Weber et al. |
| 5,802,136 A | 9/1998 | Carol |
| 5,807,386 A | 9/1998 | Slatkine et al. |
| 5,810,801 A | 9/1998 | Anderson et al. |
| 5,810,802 A | 9/1998 | Panescu et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,818,580 A | 10/1998 | Murnick |
| 5,820,625 A | 10/1998 | Izawa et al. |
| 5,820,626 A | 10/1998 | Baumgardner |
| 5,822,034 A | 10/1998 | Shimashita et al. |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,830,209 A | 11/1998 | Savage et al. |
| 5,835,648 A | 11/1998 | Narciso, Jr. et al. |
| 5,836,877 A | 11/1998 | Zavislan |
| 5,836,999 A | 11/1998 | Eckhouse et al. |
| 5,837,001 A | 11/1998 | Mackey |
| 5,840,048 A | 11/1998 | Cheng |
| 5,843,072 A | 12/1998 | Furumoto et al. |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,479 A | 2/1999 | Furumoto et al. |
| 5,871,480 A | 2/1999 | Tankovich |
| 5,879,159 A | 3/1999 | Cipolla |
| 5,879,346 A | 3/1999 | Waldman et al. |
| 5,879,376 A | 3/1999 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,893,885 A | 4/1999 | Webster, Jr. |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,908,731 A | 6/1999 | Leenders et al. |
| 5,913,883 A | 6/1999 | Alexander et al. |
| 5,916,211 A | 6/1999 | Quon et al. |
| 5,919,601 A | 7/1999 | Nguyen et al. |
| 5,920,374 A | 7/1999 | Vaphiades et al. |
| 5,921,926 A | 7/1999 | Rolland et al. |
| 5,928,222 A | 7/1999 | Kleinerman |
| 5,935,124 A | 8/1999 | Klumb et al. |
| 5,944,687 A | 8/1999 | Benett et al. |
| 5,944,748 A | 8/1999 | Mager et al. |
| 5,948,011 A | 9/1999 | Knowlton |
| 5,948,596 A | 9/1999 | Zhong et al. |
| 5,949,222 A | 9/1999 | Buono |
| 5,951,543 A | 9/1999 | Brauer |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A | 10/1999 | Fullmer et al. |
| 5,971,976 A | 10/1999 | Wang et al. |
| 5,974,059 A | 10/1999 | Dawson |
| 5,974,616 A | 11/1999 | Dreyfus |
| 5,976,123 A | 11/1999 | Baumgardner et al. |
| 5,977,723 A | 11/1999 | Yoon |
| 5,979,454 A | 11/1999 | Anvari et al. |
| 5,983,900 A | 11/1999 | Clement et al. |
| 5,984,915 A | 11/1999 | Loeb et al. |
| 6,004,723 A | 12/1999 | Figov |
| 6,007,219 A | 12/1999 | O'Meara |
| 6,015,404 A | 1/2000 | Altshuler et al. |
| 6,017,677 A | 1/2000 | Maemoto et al. |
| 6,022,316 A | 2/2000 | Eppstein et al. |
| 6,022,346 A | 2/2000 | Panescu et al. |
| 6,024,095 A | 2/2000 | Stanley, III |
| 6,026,828 A | 2/2000 | Altshuler |
| 6,027,493 A | 2/2000 | Donitzky et al. |
| 6,027,495 A | 2/2000 | Miller |
| 6,028,694 A | 2/2000 | Schmidt |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffar |
| 6,033,431 A | 3/2000 | Segal |
| 6,036,684 A | 3/2000 | Tankovich et al. |
| 6,044,514 A | 4/2000 | Kaneda et al. |
| 6,045,548 A | 4/2000 | Furumoto et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,068,963 A | 5/2000 | Aoshima |
| 6,070,092 A | 5/2000 | Kazama et al. |
| 6,071,239 A | 6/2000 | Cribbs et al. |
| 6,074,382 A | 6/2000 | Asah et al. |
| 6,077,294 A | 6/2000 | Cho et al. |
| 6,080,146 A | 6/2000 | Altshuler et al. |
| 6,080,147 A | 6/2000 | Tobinick |
| 6,083,217 A | 7/2000 | Tankovich |
| 6,086,363 A | 7/2000 | Moran et al. |
| 6,086,558 A | 7/2000 | Bower et al. |
| 6,086,580 A | 7/2000 | Mordon et al. |
| 6,090,524 A | 7/2000 | Deboer et al. |
| 6,094,767 A | 8/2000 | Iimura |
| 6,096,028 A | 8/2000 | Bahmanyar et al. |
| 6,096,029 A | 8/2000 | O'Donnell, Jr. |
| 6,096,209 A | 8/2000 | O'Brien et al. |
| 6,099,521 A | 8/2000 | Shadduck |

(56) References Cited

U.S. PATENT DOCUMENTS

| | | |
|---|---|---|
| 6,101,207 A | 8/2000 | Ilorinne |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,112,123 A | 8/2000 | Kelleher et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson et al. |
| 6,132,929 A | 10/2000 | Nakamura et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,153,352 A | 11/2000 | Oohashi et al. |
| 6,156,030 A | 12/2000 | Neev |
| 6,159,203 A | 12/2000 | Sinofsky |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,162,215 A | 12/2000 | Feng |
| 6,162,218 A | 12/2000 | Elbrecht et al. |
| 6,164,837 A | 12/2000 | Haake et al. |
| 6,171,300 B1 | 1/2001 | Adams |
| 6,171,301 B1 | 1/2001 | Nelson et al. |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,177,230 B1 | 1/2001 | Kawamura |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,190,825 B1 | 2/2001 | Denzinger et al. |
| 6,190,831 B1 | 2/2001 | Leon |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,208,458 B1 | 3/2001 | Galvanauskas et al. |
| 6,210,425 B1 | 4/2001 | Chen |
| 6,210,426 B1 | 4/2001 | Cho et al. |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,074 B1 | 5/2001 | Almeida |
| 6,228,075 B1 | 5/2001 | Furumoto |
| 6,229,831 B1 | 5/2001 | Nightingale et al. |
| 6,233,584 B1 | 5/2001 | Purcell |
| 6,235,015 B1 | 5/2001 | Mead, III et al. |
| 6,235,016 B1 | 5/2001 | Stewart |
| 6,236,891 B1 | 5/2001 | Ingle et al. |
| 6,238,839 B1 | 5/2001 | Tomita et al. |
| 6,239,442 B1 | 5/2001 | Iimura |
| 6,240,306 B1 | 5/2001 | Rohrscheib et al. |
| 6,240,925 B1 | 6/2001 | McMillan et al. |
| 6,245,093 B1 | 6/2001 | Li et al. |
| 6,245,486 B1 | 6/2001 | Teng |
| 6,246,710 B1 | 6/2001 | Furumoto et al. |
| 6,248,103 B1 | 6/2001 | Tannenbaum et al. |
| 6,248,503 B1 | 6/2001 | Vermeersch et al. |
| 6,251,127 B1 | 6/2001 | Biel |
| 6,254,388 B1 | 7/2001 | Yarborough |
| 6,261,740 B1 | 7/2001 | Nguyen et al. |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,883 B1 | 8/2001 | Furumoto |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,282,442 B1 | 8/2001 | DeStefano et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,712 B1 | 9/2001 | Nordquist et al. |
| 6,290,713 B1 | 9/2001 | Russell |
| 6,294,311 B1 | 9/2001 | Shimazu et al. |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,322,584 B2 | 11/2001 | Ingle et al. |
| 6,325,769 B1 | 12/2001 | Klopotek |
| 6,327,506 B1 | 12/2001 | Yogo et al. |
| 6,328,733 B1 | 12/2001 | Trost |
| 6,331,111 B1 | 12/2001 | Cao |
| 6,332,891 B1 | 12/2001 | Himes |
| 6,338,855 B1 | 1/2002 | Albacarys et al. |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,346,365 B1 | 2/2002 | Kawauchi et al. |
| 6,350,261 B1 | 2/2002 | Domankevitz et al. |
| 6,350,276 B1 | 2/2002 | Knowlton |
| 6,352,811 B1 | 3/2002 | Patel et al. |
| 6,354,370 B1 | 3/2002 | Miller et al. |
| 6,355,054 B1 | 3/2002 | Neuberger |
| 6,358,242 B1 | 3/2002 | Cecchetti |
| 6,358,272 B1 | 3/2002 | Wilden |
| 6,358,669 B1 | 3/2002 | Savariar-Hauck et al. |
| 6,364,872 B1 | 4/2002 | Hsia et al. |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,391,022 B1 | 5/2002 | Furumoto et al. |
| 6,394,949 B1 | 5/2002 | Crowley et al. |
| 6,395,016 B1 | 5/2002 | Oron et al. |
| 6,398,801 B1 | 6/2002 | Clement et al. |
| 6,400,011 B1 | 6/2002 | Miki |
| 6,402,739 B1 | 6/2002 | Neev |
| 6,405,732 B1 | 6/2002 | Edwards et al. |
| 6,406,474 B1 | 6/2002 | Neuberger et al. |
| 6,409,665 B1 | 6/2002 | Scott et al. |
| 6,409,723 B1 | 6/2002 | Edwards |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,423,462 B1 | 7/2002 | Kunita |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,440,633 B1 | 8/2002 | Kawauchi |
| 6,443,946 B2 | 9/2002 | Clement et al. |
| 6,443,978 B1 | 9/2002 | Zharov |
| 6,447,503 B1 | 9/2002 | Wynne et al. |
| 6,447,504 B1 | 9/2002 | Ben-Haim et al. |
| 6,451,007 B1 | 9/2002 | Koop et al. |
| 6,454,790 B1 | 9/2002 | Neuberger et al. |
| 6,459,919 B1 | 10/2002 | Lys et al. |
| 6,461,296 B1 | 10/2002 | Desai |
| 6,464,694 B1 | 10/2002 | Massengill |
| 6,468,717 B2 | 10/2002 | Kita et al. |
| 6,470,216 B1 | 10/2002 | Knowlton |
| 6,471,712 B2 | 10/2002 | Burres |
| 6,471,716 B1 | 10/2002 | Pecukonis |
| 6,475,211 B2 | 11/2002 | Chess et al. |
| 6,482,199 B1 | 11/2002 | Neev |
| 6,484,052 B1 | 11/2002 | Visuri et al. |
| 6,485,413 B1 | 11/2002 | Boppart et al. |

(56) References Cited

U.S. PATENT DOCUMENTS

| | | |
|---|---|---|
| 6,491,685 B2 | 12/2002 | Visuri et al. |
| 6,491,715 B1 | 12/2002 | Abels et al. |
| 6,493,608 B1 | 12/2002 | Niemeyer |
| 6,494,900 B1 | 12/2002 | Salansky et al. |
| 6,497,702 B1 | 12/2002 | Bernaz |
| 6,503,269 B2 | 1/2003 | Nield et al. |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,529,540 B1 | 3/2003 | Demmer et al. |
| 6,530,915 B1 | 3/2003 | Eppstein et al. |
| 6,530,916 B1 | 3/2003 | Shimmick |
| 6,537,270 B1 | 3/2003 | Elbrecht et al. |
| 6,544,257 B2 | 4/2003 | Nagase et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,580,732 B1 | 6/2003 | Guch, Jr. et al. |
| 6,595,934 B1 | 7/2003 | Hissong et al. |
| 6,600,951 B1 | 7/2003 | Anderson |
| 6,602,245 B1 | 8/2003 | Thiberg |
| 6,602,275 B1 | 8/2003 | Sullivan |
| 6,603,988 B2 | 8/2003 | Dowlatshahi |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,607,525 B2 | 8/2003 | Franco |
| 6,610,052 B2 | 8/2003 | Furumoto |
| 6,613,040 B2 | 9/2003 | Tankovich et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,666,856 B2 | 12/2003 | Connors et al. |
| 6,669,685 B1 | 12/2003 | Rizoiu et al. |
| 6,675,425 B1 | 1/2004 | Iimura |
| 6,676,654 B1 | 1/2004 | Balle-Petersen et al. |
| 6,679,837 B2 | 1/2004 | Daikuzono |
| 6,682,523 B2 | 1/2004 | Shadduck |
| 6,682,524 B1 | 1/2004 | Elbrecht et al. |
| 6,685,639 B1 | 2/2004 | Wang et al. |
| 6,685,699 B1 | 2/2004 | Eppstein et al. |
| 6,685,722 B1 | 2/2004 | Rosenbluth et al. |
| 6,689,124 B1 | 2/2004 | Thiberg |
| 6,692,456 B1 | 2/2004 | Eppstein et al. |
| 6,692,517 B2 | 2/2004 | Cho et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,724,958 B2 | 4/2004 | German et al. |
| 6,726,681 B2 | 4/2004 | Grasso, III et al. |
| 6,736,807 B2 | 5/2004 | Yamazaki et al. |
| 6,743,222 B2 | 6/2004 | Durkin et al. |
| 6,746,444 B2 | 6/2004 | Key |
| 6,749,623 B1 | 6/2004 | Hsi et al. |
| 6,755,647 B2 | 6/2004 | Melikechi et al. |
| 6,770,069 B1 | 8/2004 | Hobart et al. |
| 6,772,053 B2 | 8/2004 | Niemeyer |
| 6,790,205 B1 | 9/2004 | Yamazaki et al. |
| 6,800,122 B2 | 10/2004 | Anderson et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| 6,824,542 B2 | 11/2004 | Jay |
| RE38,670 E | 12/2004 | Asah et al. |
| 6,858,009 B2 | 2/2005 | Kawata et al. |
| 6,860,879 B2 | 3/2005 | Irion et al. |
| 6,860,896 B2 | 3/2005 | Leber et al. |
| 6,862,771 B1 | 3/2005 | Muller |
| 6,863,781 B2 | 3/2005 | Nocera et al. |
| 6,872,203 B2 | 3/2005 | Shafirstein et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,905,492 B2 | 6/2005 | Zvuloni et al. |
| 6,916,316 B2 | 7/2005 | Jay |
| 6,936,046 B2 | 8/2005 | Hissong et al. |
| 6,942,658 B1 | 9/2005 | Rizoiu et al. |
| 6,953,341 B2 | 10/2005 | Black |
| 6,974,450 B2 | 12/2005 | Weber et al. |
| 6,974,451 B2 | 12/2005 | Altshuler et al. |
| 6,976,985 B2 | 12/2005 | Altshuler et al. |
| 6,986,903 B2 | 1/2006 | Zulli et al. |
| 6,989,007 B2 | 1/2006 | Shadduck |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,006,540 B2 | 2/2006 | Rieger |
| 7,006,874 B2 | 2/2006 | Knowlton et al. |
| 7,018,396 B2 | 3/2006 | Sierra et al. |
| 7,029,469 B2 | 4/2006 | Vasily |
| 7,033,349 B2 | 4/2006 | Key |
| 7,036,516 B1 | 5/2006 | Dees et al. |
| 7,041,094 B2 | 5/2006 | Connors et al. |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,104,985 B2 | 9/2006 | Martinelli |
| 7,118,562 B2 | 10/2006 | Furumoto |
| 7,118,563 B2 | 10/2006 | Weckwerth et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,170,034 B2 | 1/2007 | Shalev et al. |
| 7,175,617 B2 | 2/2007 | Jay |
| 7,182,760 B2 | 2/2007 | Kubota |
| 7,198,634 B2 | 4/2007 | Harth et al. |

(56) References Cited

U.S. PATENT DOCUMENTS

| | | |
|---|---|---|
| 7,202,446 B2 | 4/2007 | Shalev et al. |
| 7,204,832 B2 | 4/2007 | Altshuler et al. |
| 7,216,055 B1 | 5/2007 | Horton et al. |
| 7,217,265 B2 | 5/2007 | Hennings et al. |
| 7,217,267 B2 | 5/2007 | Jay |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,280,866 B1 | 10/2007 | McIntosh et al. |
| 7,282,060 B2 | 10/2007 | DeBenedictis et al. |
| 7,282,723 B2 | 10/2007 | Schomacker et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,333,841 B2 | 2/2008 | Maruo et al. |
| 7,351,252 B2 | 4/2008 | Altshuler et al. |
| 7,354,448 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler et al. |
| 7,436,863 B2 | 10/2008 | Matsuda et al. |
| 7,500,956 B1 | 3/2009 | Wilk |
| 7,531,967 B2 | 5/2009 | Inochkin et al. |
| 7,540,869 B2 | 6/2009 | Altshuler et al. |
| 7,553,308 B2 | 6/2009 | Jay |
| 7,586,957 B2 | 9/2009 | Sierra et al. |
| 7,588,547 B2 | 9/2009 | Deem et al. |
| 7,624,640 B2 | 12/2009 | Maris et al. |
| 7,647,092 B2 | 1/2010 | Motz et al. |
| 7,699,058 B1 | 4/2010 | Jay |
| 7,722,600 B2 | 5/2010 | Connors et al. |
| 7,758,621 B2 | 7/2010 | Altshuler et al. |
| 7,763,016 B2 | 7/2010 | Altshuler et al. |
| 7,839,972 B2 | 11/2010 | Ruchala et al. |
| 7,856,985 B2 | 12/2010 | Mirkov et al. |
| 7,860,554 B2 | 12/2010 | Leonardi et al. |
| 7,929,579 B2 | 4/2011 | Hohm et al. |
| 7,931,028 B2 | 4/2011 | Jay |
| 7,935,107 B2 | 5/2011 | Altshuler et al. |
| 7,938,821 B2 | 5/2011 | Chan et al. |
| 7,942,869 B2 | 5/2011 | Houbolt et al. |
| 7,942,915 B2 | 5/2011 | Altshuler et al. |
| 7,942,916 B2 | 5/2011 | Altshuler et al. |
| 7,998,181 B2 | 8/2011 | Nightingale et al. |
| 8,002,768 B1 | 8/2011 | Altshuler et al. |
| 8,027,710 B1 | 9/2011 | Dannan |
| 8,109,924 B2 | 2/2012 | Altshuler et al. |
| 8,113,209 B2 | 2/2012 | Masotti et al. |
| 8,182,473 B2 | 5/2012 | Altshuler et al. |
| 8,317,779 B2 | 11/2012 | Mirkov et al. |
| 8,322,348 B2 | 12/2012 | Mirkov et al. |
| 8,328,794 B2 | 12/2012 | Altshuler et al. |
| 8,328,796 B2 | 12/2012 | Altshuler et al. |
| 8,346,347 B2 | 1/2013 | Altshuler et al. |
| 8,357,145 B2 | 1/2013 | Schleicher et al. |
| 8,378,322 B2 | 2/2013 | Dahm et al. |
| 8,439,940 B2 | 5/2013 | Chomas et al. |
| 10,849,687 B2 * | 12/2020 | Sierra ........................ H01S 3/00 |
| 10,966,785 B2 * | 4/2021 | Sierra ........................ H01S 3/00 |
| 2001/0007068 A1 | 7/2001 | Ota et al. |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0029956 A1 | 10/2001 | Argenta et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0002367 A1 | 1/2002 | Tankovich et al. |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0015911 A1 | 2/2002 | Nakamura |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0019625 A1 | 2/2002 | Azar |
| 2002/0026225 A1 | 2/2002 | Segal |
| 2002/0028404 A1 | 3/2002 | Nakamura |
| 2002/0029071 A1 | 3/2002 | Whitehurst |
| 2002/0032437 A1 | 3/2002 | Andrews et al. |
| 2002/0039702 A1 | 4/2002 | Hotta |
| 2002/0045891 A1 | 4/2002 | Clement et al. |
| 2002/0048722 A1 | 4/2002 | Aoshima |
| 2002/0049432 A1 | 4/2002 | Mukai |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111546 A1 | 8/2002 | Cook et al. |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0125230 A1 | 9/2002 | Haight et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0128696 A1 | 9/2002 | Pearl et al. |
| 2002/0151878 A1 | 10/2002 | Shimmick et al. |
| 2002/0151879 A1 | 10/2002 | Loeb |
| 2002/0160299 A1 | 10/2002 | Asawa et al. |
| 2002/0161357 A1 | 10/2002 | Anderson et al. |
| 2002/0161418 A1 | 10/2002 | Wilkens et al. |
| 2002/0167974 A1 | 11/2002 | Kennedy et al. |
| 2002/0173723 A1 | 11/2002 | Lewis et al. |
| 2002/0173777 A1 | 11/2002 | Sand |
| 2002/0173780 A1 | 11/2002 | Altshuler et al. |
| 2002/0173781 A1 | 11/2002 | Cense et al. |
| 2002/0173782 A1 | 11/2002 | Cense et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0004556 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028186 A1 | 2/2003 | Kreindel |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055413 A1 | 3/2003 | Altshuler et al. |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0073989 A1 | 4/2003 | Hoey et al. |
| 2003/0083649 A1 | 5/2003 | Margaron et al. |
| 2003/0084534 A1 | 5/2003 | Kaizuka |
| 2003/0092982 A1 | 5/2003 | Eppstein |
| 2003/0097122 A1 | 5/2003 | Ganz et al. |
| 2003/0100936 A1 | 5/2003 | Altshuler et al. |
| 2003/0104340 A1 | 6/2003 | Clemans |

(56) References Cited

U.S. PATENT DOCUMENTS

| | | |
|---|---|---|
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0158550 A1 | 8/2003 | Ganz et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187319 A1 | 10/2003 | Kaneko et al. |
| 2003/0187383 A1 | 10/2003 | Weber et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | Debenedictis et al. |
| 2003/0216795 A1 | 11/2003 | Harth et al. |
| 2003/0232303 A1 | 12/2003 | Black |
| 2003/0233138 A1 | 12/2003 | Spooner |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0054248 A1 | 3/2004 | Kimchy et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0098070 A1 | 5/2004 | Mohr et al. |
| 2004/0105611 A1 | 6/2004 | Bischel et al. |
| 2004/0111031 A1 | 6/2004 | Alfano et al. |
| 2004/0111086 A1 | 6/2004 | Trembly |
| 2004/0111132 A1 | 6/2004 | Shenderova et al. |
| 2004/0116984 A1 | 6/2004 | Spooner et al. |
| 2004/0122311 A1 | 6/2004 | Cosman |
| 2004/0133251 A1 | 7/2004 | Altshuler et al. |
| 2004/0143181 A1 | 7/2004 | Damasco et al. |
| 2004/0143247 A1 | 7/2004 | Anderson et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162490 A1 | 8/2004 | Soltz et al. |
| 2004/0162549 A1 | 8/2004 | Altshuler |
| 2004/0162596 A1 | 8/2004 | Altshuler et al. |
| 2004/0167502 A1 | 8/2004 | Weckwerth et al. |
| 2004/0176754 A1 | 9/2004 | Island et al. |
| 2004/0176764 A1 | 9/2004 | Dant |
| 2004/0181211 A1 | 9/2004 | Graham et al. |
| 2004/0186465 A1 | 9/2004 | Francischelli et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199079 A1 | 10/2004 | Chuck et al. |
| 2004/0199151 A1 | 10/2004 | Neuberger |
| 2004/0199227 A1 | 10/2004 | Altshuler et al. |
| 2004/0204745 A1 | 10/2004 | Altshuler et al. |
| 2004/0208918 A1 | 10/2004 | Koch et al. |
| 2004/0210275 A1 | 10/2004 | Town et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0249261 A1 | 12/2004 | Torchia et al. |
| 2004/0254567 A1 | 12/2004 | Holz et al. |
| 2004/0260210 A1 | 12/2004 | Ella et al. |
| 2005/0015077 A1 | 1/2005 | Kuklin et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065502 A1 | 3/2005 | Stoltz |
| 2005/0065531 A1 | 3/2005 | Cohen |
| 2005/0074038 A1 | 4/2005 | Khaydarov |
| 2005/0080404 A1 | 4/2005 | Jones et al. |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143719 A1 | 6/2005 | Sink |
| 2005/0143723 A1 | 6/2005 | Zvuloni et al. |
| 2005/0154380 A1 | 7/2005 | DeBenedictis et al. |
| 2005/0165315 A1 | 7/2005 | Zuluaga et al. |
| 2005/0165393 A1 | 7/2005 | Eppstein |
| 2005/0168158 A1 | 8/2005 | Inochkin et al. |
| 2005/0170313 A1 | 8/2005 | Pitz et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0177139 A1 | 8/2005 | Yamazaki et al. |
| 2005/0177142 A1 | 8/2005 | Jay |
| 2005/0182389 A1 | 8/2005 | LaPorte et al. |
| 2005/0197681 A1 | 9/2005 | Barolet et al. |
| 2005/0203496 A1 | 9/2005 | Ritchie et al. |
| 2005/0203497 A1 | 9/2005 | Speeg et al. |
| 2005/0215988 A1 | 9/2005 | Altshuler et al. |
| 2005/0220726 A1 | 10/2005 | Pauly et al. |
| 2005/0222556 A1 | 10/2005 | Ariura et al. |
| 2005/0245917 A1 | 11/2005 | Strassl et al. |
| 2005/0251116 A1 | 11/2005 | Steinke et al. |
| 2005/0251117 A1 | 11/2005 | Anderson et al. |
| 2005/0251118 A1 | 11/2005 | Anderson et al. |
| 2005/0251120 A1 | 11/2005 | Anderson et al. |
| 2005/0257612 A1 | 11/2005 | Hiemer et al. |
| 2005/0281530 A1 | 12/2005 | Rizoiu et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0009750 A1 | 1/2006 | Altshuler et al. |
| 2006/0013533 A1 | 1/2006 | Slatkine |
| 2006/0020309 A1 | 1/2006 | Altshuler et al. |
| 2006/0047281 A1 | 3/2006 | Kreindel |
| 2006/0052661 A1 | 3/2006 | Gannot et al. |
| 2006/0056589 A1 | 3/2006 | Engelward |
| 2006/0058712 A1 | 3/2006 | Altshuler et al. |
| 2006/0062448 A1 | 3/2006 | Hirsch et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0095101 A1 | 5/2006 | Dees et al. |
| 2006/0100677 A1 | 5/2006 | Blumenkranz et al. |
| 2006/0116671 A1 | 6/2006 | Slayton et al. |
| 2006/0118127 A1 | 6/2006 | Chinn |
| 2006/0122584 A1 | 6/2006 | Bommannan et al. |
| 2006/0122668 A1 | 6/2006 | Anderson et al. |
| 2006/0128771 A1 | 6/2006 | Mirkov et al. |
| 2006/0149343 A1 | 7/2006 | Altshuler et al. |
| 2006/0155266 A1 | 7/2006 | Manstein et al. |
| 2006/0161143 A1 | 7/2006 | Altshuler et al. |
| 2006/0173480 A1 | 8/2006 | Zhang |
| 2006/0194164 A1 | 8/2006 | Altshuler et al. |
| 2006/0206103 A1 | 9/2006 | Altshuler et al. |
| 2006/0217689 A1 | 9/2006 | Dick et al. |
| 2006/0224148 A1 | 10/2006 | Cho et al. |
| 2006/0247609 A1 | 11/2006 | Mirkov et al. |
| 2006/0253176 A1 | 11/2006 | Caruso et al. |

(56) References Cited

U.S. PATENT DOCUMENTS

| | | |
|---|---|---|
| 2006/0259102 A1 | 11/2006 | Slatkine |
| 2006/0265032 A1 | 11/2006 | Hennings et al. |
| 2006/0271028 A1 | 11/2006 | Altshuler et al. |
| 2006/0282067 A1 | 12/2006 | Koop et al. |
| 2006/0287646 A1 | 12/2006 | Altshuler et al. |
| 2006/0293727 A1 | 12/2006 | Spooner et al. |
| 2006/0293728 A1 | 12/2006 | Roersma et al. |
| 2007/0027440 A1 | 2/2007 | Altshuler et al. |
| 2007/0038206 A1 | 2/2007 | Altshuler et al. |
| 2007/0038271 A1 | 2/2007 | Cole et al. |
| 2007/0049910 A1 | 3/2007 | Altshuler et al. |
| 2007/0060819 A1 | 3/2007 | Altshuler et al. |
| 2007/0060989 A1 | 3/2007 | Deem et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0088206 A1 | 4/2007 | Peyman et al. |
| 2007/0093797 A1 | 4/2007 | Chan et al. |
| 2007/0105212 A1 | 5/2007 | Oldham et al. |
| 2007/0121069 A1 | 5/2007 | Andersen et al. |
| 2007/0123851 A1 | 5/2007 | Alejandro et al. |
| 2007/0142881 A1 | 6/2007 | Hennings |
| 2007/0159592 A1 | 7/2007 | Rylander et al. |
| 2007/0173749 A1 | 7/2007 | Williams et al. |
| 2007/0179378 A1 | 8/2007 | Boese et al. |
| 2007/0179470 A1 | 8/2007 | Toombs |
| 2007/0185552 A1 | 8/2007 | Masotti et al. |
| 2007/0191827 A1 | 8/2007 | Lischinsky et al. |
| 2007/0194717 A1 | 8/2007 | Belikov |
| 2007/0198004 A1 | 8/2007 | Altshuler et al. |
| 2007/0208252 A1 | 9/2007 | Makower |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0213851 A1 | 9/2007 | Bellas et al. |
| 2007/0219602 A1 | 9/2007 | Ostrovsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0244527 A1 | 10/2007 | Hatayama et al. |
| 2007/0255355 A1 | 11/2007 | Altshuler et al. |
| 2007/0260230 A1 | 11/2007 | Youngquist et al. |
| 2007/0264625 A1 | 11/2007 | DeBenedictis et al. |
| 2007/0280305 A1 | 12/2007 | Zucker |
| 2007/0288071 A1 | 12/2007 | Rogers |
| 2008/0003536 A1 | 1/2008 | Altshuler et al. |
| 2008/0004608 A1 | 1/2008 | Dacquay et al. |
| 2008/0004611 A1 | 1/2008 | Houbolt et al. |
| 2008/0009842 A1 | 1/2008 | Manstein et al. |
| 2008/0033516 A1 | 2/2008 | Altshuler et al. |
| 2008/0058782 A1 | 3/2008 | Frangineas et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0154247 A1 | 6/2008 | Dallarosa et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0194969 A1 | 8/2008 | Werahera et al. |
| 2008/0195183 A1 | 8/2008 | Botchkareva et al. |
| 2008/0208105 A1 | 8/2008 | Zelickson et al. |
| 2008/0214988 A1 | 9/2008 | Altshuler et al. |
| 2008/0215038 A1 | 9/2008 | Bakker et al. |
| 2008/0248554 A1 | 10/2008 | Merchant et al. |
| 2008/0262577 A1 | 10/2008 | Altshuler et al. |
| 2008/0294150 A1 | 11/2008 | Altshuler et al. |
| 2008/0294152 A1 | 11/2008 | Altshuler et al. |
| 2008/0294153 A1 | 11/2008 | Altshuler et al. |
| 2008/0306471 A1 | 12/2008 | Altshuler et al. |
| 2008/0319430 A1 | 12/2008 | Zenzie et al. |
| 2009/0018531 A1 | 1/2009 | Welches et al. |
| 2009/0018624 A1 | 1/2009 | Levinson et al. |
| 2009/0024023 A1 | 1/2009 | Welches et al. |
| 2009/0024192 A1 | 1/2009 | Mulholland |
| 2009/0024193 A1 | 1/2009 | Altshuler et al. |
| 2009/0043294 A1 | 2/2009 | Island et al. |
| 2009/0048557 A1 | 2/2009 | Yeshurun et al. |
| 2009/0069741 A1 | 3/2009 | Altshuler et al. |
| 2009/0132011 A1 | 5/2009 | Altshuler et al. |
| 2009/0137995 A1 | 5/2009 | Altshuler et al. |
| 2009/0149843 A1 | 6/2009 | Smits et al. |
| 2009/0149844 A1 | 6/2009 | Altshuler et al. |
| 2009/0222068 A1 | 9/2009 | Oberreiter et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2009/0292277 A1 | 11/2009 | Sierra et al. |
| 2009/0312749 A1 | 12/2009 | Pini et al. |
| 2010/0010507 A1 | 1/2010 | Kinoshita et al. |
| 2010/0015576 A1 | 1/2010 | Altshuler et al. |
| 2010/0021867 A1 | 1/2010 | Altshuler et al. |
| 2010/0036295 A1 | 2/2010 | Altshuler et al. |
| 2010/0049180 A1 | 2/2010 | Wells et al. |
| 2010/0109041 A1 | 5/2010 | Yin et al. |
| 2010/0123399 A1 | 5/2010 | Bollmann et al. |
| 2010/0145321 A1 | 6/2010 | Altshuler et al. |
| 2010/0195680 A1 | 8/2010 | Sierra et al. |
| 2010/0198134 A1 | 8/2010 | Eckhouse et al. |
| 2010/0204686 A1 | 8/2010 | Yaroslavksy et al. |
| 2010/0217248 A1 | 8/2010 | Mirkov et al. |
| 2010/0278756 A1 | 11/2010 | Chung et al. |
| 2010/0286673 A1 | 11/2010 | Altshuler et al. |
| 2010/0298744 A1 | 11/2010 | Altshuler et al. |
| 2011/0046523 A1 | 2/2011 | Altshuler et al. |
| 2011/0087155 A1 | 4/2011 | Uhland et al. |
| 2011/0118722 A1 | 5/2011 | Lischinsky et al. |
| 2011/0137230 A1 | 6/2011 | Altshuler et al. |
| 2011/0152847 A1 | 6/2011 | Mirkov et al. |
| 2011/0172651 A1 | 7/2011 | Altshuler et al. |
| 2011/0184334 A1 | 7/2011 | Altshuler et al. |
| 2011/0207075 A1 | 8/2011 | Altshuler et al. |
| 2011/0257584 A1 | 10/2011 | Altshuler et al. |
| 2011/0267830 A1 | 11/2011 | Altshuler et al. |
| 2011/0313408 A1 | 12/2011 | Tankovich et al. |
| 2012/0022510 A1 | 1/2012 | Welches et al. |
| 2012/0023129 A1 | 1/2012 | Vedula et al. |
| 2012/0083862 A1 | 4/2012 | Altshuler et al. |
| 2012/0099816 A1 | 4/2012 | Wilson |
| 2012/0116271 A1 | 5/2012 | Caruso et al. |
| 2012/0123399 A1 | 5/2012 | Belikov et al. |
| 2012/0165725 A1 | 6/2012 | Chomas et al. |
| 2012/0277659 A1 | 11/2012 | Yaroslavsky et al. |
| 2012/0301842 A1 | 11/2012 | Altshuler et al. |

FOREIGN PATENT DOCUMENTS

| | | |
|---|---|---|
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| DE | 2826383 A1 | 12/1979 |
| DE | 3304230 A1 | 8/1984 |
| DE | 3719561 A1 | 1/1988 |
| DE | 8807746 U1 | 9/1988 |
| DE | 8837248 A1 | 5/1990 |
| DE | 3841503 A1 | 6/1990 |
| DE | 9102407 U1 | 7/1991 |
| DE | 19803460 C1 | 8/1999 |
| DE | 19944401 A1 | 3/2001 |
| DE | 10140715 A1 | 3/2002 |
| DE | 10112289 A1 | 9/2002 |
| DE | 10120787 A1 | 1/2003 |
| EP | 0000593 A1 | 2/1979 |
| EP | 0142671 A1 | 5/1985 |
| EP | 0172490 A1 | 2/1986 |
| EP | 0297360 A1 | 1/1989 |
| EP | 0320080 A1 | 6/1989 |

(56) References Cited

FOREIGN PATENT DOCUMENTS

| | | |
|---|---|---|
| EP | 0324120 A1 | 7/1989 |
| EP | 0413025 A1 | 2/1991 |
| EP | 0458576 A2 | 11/1991 |
| EP | 0563953 A2 | 10/1993 |
| EP | 0565331 A2 | 10/1993 |
| EP | 0575274 A1 | 12/1993 |
| EP | 0593375 A1 | 4/1994 |
| EP | 0598984 A1 | 6/1994 |
| EP | 0709941 A1 | 5/1996 |
| EP | 0724894 A2 | 8/1996 |
| EP | 0726083 A2 | 8/1996 |
| EP | 0736308 A2 | 10/1996 |
| EP | 0743029 A2 | 11/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 0884066 A2 | 12/1998 |
| EP | 0885629 A2 | 12/1998 |
| EP | 0920840 A2 | 6/1999 |
| EP | 0927544 A2 | 7/1999 |
| EP | 0949730 A2 | 10/1999 |
| EP | 1031414 A1 | 8/2000 |
| EP | 1038505 A2 | 9/2000 |
| EP | 1057454 A2 | 12/2000 |
| EP | 1057455 A2 | 12/2000 |
| EP | 1072402 A2 | 1/2001 |
| EP | 1075854 A2 | 2/2001 |
| EP | 1138269 A1 | 10/2001 |
| EP | 1138349 A2 | 10/2001 |
| EP | 1147785 A2 | 10/2001 |
| EP | 1219258 A1 | 7/2002 |
| EP | 1226787 A2 | 7/2002 |
| EP | 1238683 A1 | 9/2002 |
| EP | 1250893 A2 | 10/2002 |
| EP | 1457234 A2 | 9/2004 |
| EP | 1495735 A1 | 1/2005 |
| EP | 1512373 A1 | 3/2005 |
| EP | 1535582 A1 | 6/2005 |
| EP | 1627662 A1 | 2/2006 |
| EP | 1650615 A1 | 4/2006 |
| EP | 1797836 A1 | 6/2007 |
| EP | 1839705 A1 | 10/2007 |
| EP | 1854505 A2 | 11/2007 |
| FR | 1251424 A | 1/1961 |
| FR | 2199453 A1 | 4/1974 |
| FR | 2591902 A1 | 6/1987 |
| GB | 1251424 A | 10/1971 |
| GB | 1274017 A | 5/1972 |
| GB | 1546625 A | 5/1979 |
| GB | 2044908 A | 10/1980 |
| GB | 2059053 A | 4/1981 |
| GB | 2059054 A | 4/1981 |
| GB | 2123287 A | 2/1984 |
| GB | 2212010 A | 7/1989 |
| GB | 2239675 A | 7/1991 |
| GB | 2270159 A | 3/1994 |
| GB | 2356570 A | 5/2001 |
| GB | 2360461 A | 9/2001 |
| GB | 2360946 A | 10/2001 |
| GB | 2364376 A | 1/2002 |
| GB | 2368020 A | 4/2002 |
| GB | 2390021 A | 12/2003 |
| GB | 2397528 A | 7/2004 |
| JP | S54129791 A | 10/1979 |
| JP | S5552766 A | 4/1980 |
| JP | S5577187 A | 6/1980 |
| JP | S574007 A | 1/1982 |
| JP | S62165985 A | 7/1987 |
| JP | S6323648 A | 1/1988 |
| JP | S63249577 A | 10/1988 |
| JP | S6427554 A | 1/1989 |
| JP | S6481222 A | 3/1989 |
| JP | H0199574 A | 4/1989 |
| JP | H01181877 A | 7/1989 |
| JP | H02199 | 1/1990 |
| JP | H022199 A | 1/1990 |
| JP | H0285694 A | 3/1990 |
| JP | H02174804 A | 7/1990 |
| JP | H02285694 A | 11/1990 |
| JP | H0316956 A | 1/1991 |
| JP | H0319385 A | 1/1991 |
| JP | H0366387 A | 3/1991 |
| JP | H03183184 A | 8/1991 |
| JP | H03281390 A | 12/1991 |
| JP | H0622871 A | 2/1994 |
| JP | H06154239 A | 6/1994 |
| JP | H079179 A | 1/1995 |
| JP | H0763957 A | 3/1995 |
| JP | H07328025 A | 12/1995 |
| JP | H0815539 A | 1/1996 |
| JP | H0854538 A | 2/1996 |
| JP | H0984803 A | 3/1997 |
| JP | H09141869 A | 6/1997 |
| JP | H9220292 A | 8/1997 |
| JP | H1014661 A | 1/1998 |
| JP | H1147146 A | 2/1999 |
| JP | H11232229 A | 8/1999 |
| JP | 2000037400 A | 2/2000 |
| JP | 2000153003 A | 6/2000 |
| JP | 2000300684 A | 10/2000 |
| JP | 2001000560 A | 1/2001 |
| JP | 2001029124 A | 2/2001 |
| JP | 2001145520 A | 5/2001 |
| JP | 2001196665 A | 7/2001 |
| JP | 2001343560 A | 12/2001 |
| JP | 2002272861 A | 9/2002 |
| JP | 2003052843 A | 2/2003 |
| JP | 2005017796 A | 1/2005 |
| JP | 2005027702 A | 2/2005 |
| JP | 2006192073 A | 7/2006 |
| RU | 2082337 C1 | 6/1997 |
| RU | 2089126 C1 | 9/1997 |
| RU | 2089127 C1 | 9/1997 |
| RU | 2096051 C1 | 11/1997 |
| RU | 2122848 C1 | 12/1998 |
| WO | 8602783 A1 | 5/1986 |
| WO | 8804592 A1 | 6/1988 |
| WO | 9000420 A1 | 1/1990 |
| WO | 9006727 A1 | 6/1990 |
| WO | 9012548 A1 | 11/1990 |
| WO | 9101053 A1 | 1/1991 |
| WO | 9102562 A1 | 3/1991 |
| WO | 9112050 A1 | 8/1991 |
| WO | 9113652 A1 | 9/1991 |
| WO | 9113653 A1 | 9/1991 |
| WO | 9118646 A1 | 12/1991 |
| WO | 9203977 A2 | 3/1992 |
| WO | 9206739 A1 | 4/1992 |
| WO | 9216338 A1 | 10/1992 |
| WO | 9219165 A1 | 11/1992 |
| WO | 9305920 A1 | 4/1993 |
| WO | 9321843 A1 | 11/1993 |
| WO | 9503089 A1 | 2/1995 |
| WO | 9504393 A2 | 2/1995 |
| WO | 9510243 A1 | 4/1995 |
| WO | 9514251 A1 | 5/1995 |
| WO | 9515725 A1 | 6/1995 |
| WO | 9532441 A1 | 11/1995 |
| WO | 9533518 A1 | 12/1995 |
| WO | 9609853 A1 | 4/1996 |
| WO | 9618347 A1 | 6/1996 |
| WO | 9622741 A1 | 8/1996 |
| WO | 9622813 A1 | 8/1996 |
| WO | 9623447 A1 | 8/1996 |
| WO | 9624182 A1 | 8/1996 |
| WO | 9624406 A1 | 8/1996 |
| WO | 9625979 A1 | 8/1996 |
| WO | 9628212 A1 | 9/1996 |
| WO | 1996034316 A1 | 10/1996 |
| WO | 9636396 A2 | 11/1996 |
| WO | 9639734 A1 | 12/1996 |
| WO | 9641579 A1 | 12/1996 |

(56) References Cited

FOREIGN PATENT DOCUMENTS

| | | |
|---|---|---|
| WO | 1997000777 A2 | 1/1997 |
| WO | 9713458 A1 | 4/1997 |
| WO | 9713552 A1 | 4/1997 |
| WO | 9722384 A1 | 6/1997 |
| WO | 9728752 A1 | 8/1997 |
| WO | 9737602 A2 | 10/1997 |
| WO | 9737723 A1 | 10/1997 |
| WO | 9804317 A1 | 2/1998 |
| WO | 9805286 A1 | 2/1998 |
| WO | 9805380 A1 | 2/1998 |
| WO | 9806456 A1 | 2/1998 |
| WO | 9807379 A1 | 2/1998 |
| WO | 9820937 A2 | 5/1998 |
| WO | 9824507 A2 | 6/1998 |
| WO | 9829134 A2 | 7/1998 |
| WO | 9841158 A1 | 9/1998 |
| WO | 9851235 A1 | 11/1998 |
| WO | 9852481 A1 | 11/1998 |
| WO | 9858595 A1 | 12/1998 |
| WO | 9910046 A1 | 3/1999 |
| WO | 9917666 A1 | 4/1999 |
| WO | 9917667 A1 | 4/1999 |
| WO | 9917668 A1 | 4/1999 |
| WO | 9927997 A1 | 6/1999 |
| WO | 9929243 A1 | 6/1999 |
| WO | 9934867 A1 | 7/1999 |
| WO | 9938569 A2 | 8/1999 |
| WO | 9939410 A1 | 8/1999 |
| WO | 9943387 A1 | 9/1999 |
| WO | 9944638 A1 | 9/1999 |
| WO | 9946005 A1 | 9/1999 |
| WO | 9949937 A1 | 10/1999 |
| WO | 9958195 A1 | 11/1999 |
| WO | 9962472 A1 | 12/1999 |
| WO | 9966988 A1 | 12/1999 |
| WO | 0002491 A1 | 1/2000 |
| WO | 0003257 A1 | 1/2000 |
| WO | 0007514 A1 | 2/2000 |
| WO | 0030714 A1 | 6/2000 |
| WO | 0032272 A1 | 6/2000 |
| WO | 0040266 A2 | 7/2000 |
| WO | 0041278 A1 | 7/2000 |
| WO | 0043070 A1 | 7/2000 |
| WO | 0044294 A1 | 8/2000 |
| WO | 0053113 A1 | 9/2000 |
| WO | 0054649 A2 | 9/2000 |
| WO | 0054685 A2 | 9/2000 |
| WO | 0062700 A1 | 10/2000 |
| WO | 0064537 A1 | 11/2000 |
| WO | 0066226 A1 | 11/2000 |
| WO | 0071045 A1 | 11/2000 |
| WO | 0074583 A1 | 12/2000 |
| WO | 0074781 A1 | 12/2000 |
| WO | 0078242 A1 | 12/2000 |
| WO | 0103257 A1 | 1/2001 |
| WO | 0114012 A1 | 3/2001 |
| WO | 0126573 A1 | 4/2001 |
| WO | 0134048 A1 | 5/2001 |
| WO | 0150963 A1 | 7/2001 |
| WO | 0154606 A1 | 8/2001 |
| WO | 0154770 A1 | 8/2001 |
| WO | 0178830 A2 | 10/2001 |
| WO | 0209813 A1 | 2/2002 |
| WO | 0226147 A1 | 4/2002 |
| WO | 02053050 A1 | 7/2002 |
| WO | 02069825 A2 | 9/2002 |
| WO | 02078559 A1 | 10/2002 |
| WO | 02094116 A1 | 11/2002 |
| WO | 03005883 A2 | 1/2003 |
| WO | 03049633 A1 | 6/2003 |
| WO | 03103529 A1 | 12/2003 |
| WO | 2004000150 A1 | 12/2003 |
| WO | 2004011848 A2 | 2/2004 |
| WO | 2004033040 A1 | 4/2004 |
| WO | 2004037068 A2 | 5/2004 |
| WO | 2004037287 A2 | 5/2004 |
| WO | 2004073537 A2 | 9/2004 |
| WO | 2004080279 A2 | 9/2004 |
| WO | 2004084752 A2 | 10/2004 |
| WO | 2004086947 A2 | 10/2004 |
| WO | 2005007003 A1 | 1/2005 |
| WO | 2005009266 A1 | 2/2005 |
| WO | 2005030317 A2 | 4/2005 |
| WO | 2005046793 A2 | 5/2005 |
| WO | 2005065288 A2 | 7/2005 |
| WO | 2005092438 A1 | 10/2005 |
| WO | 2005096981 A2 | 10/2005 |
| WO | 2005099369 A2 | 10/2005 |
| WO | 2005112815 A1 | 12/2005 |
| WO | 2006006123 A1 | 1/2006 |
| WO | 2006036968 A2 | 4/2006 |
| WO | 2006066226 A1 | 6/2006 |
| WO | 2006089227 A2 | 8/2006 |
| WO | 2006101735 A1 | 9/2006 |
| WO | 2006116141 A1 | 11/2006 |
| WO | 2007035444 A2 | 3/2007 |
| WO | 2007122611 A2 | 11/2007 |
| WO | 2008007218 A2 | 1/2008 |
| WO | 2008070747 A2 | 6/2008 |
| WO | 2008153999 A1 | 12/2008 |
| WO | 2010102255 A1 | 9/2010 |
| WO | 2012023129 A1 | 2/2012 |

OTHER PUBLICATIONS

Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Osigo et al., "Phase Transitions of Rat Stratum Corneum Lipids by an Electron Paramagnetic Resonance Study and Relationship of Phase States to Drug Penetration," Biochimica et Biophysica Acta 1301:97-104 (1996).
Overholt BF et al. "Balloon photodynamic therapy of esophageal cancer: effect of increasing balloon size." PubMed; Lasers Surg Med. 1996, 18(3):248-52.
Ozawa et al., "Stimulatory Effects of Low-Power Laser Irradiation on Bone Formation in vitro," SPIE vol. 1984, pp. 281-288.
Panjehpour M et al. "Spectroscopic diagnosis of esophageal cancer: new classification model, improved measurement system." PubMed; Gastrointest Endosc. Jun. 1995, 41 (6):577-81.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polanyi, Thomas & Tobias, Irwin, Lasers—A Series of Advances, Edited by A.K. Levine, vol. 2, Marcel Dekker, Inc, N.Y., 1968, pp. 400, 402-403 & 422.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Reed J.T. et al., "Treatment of Periorbital Wrinkles," Washington Inst. of Dermatol. Surg. 23:643-648 (1997).
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).

(56) References Cited

OTHER PUBLICATIONS

Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy Of A Novel Light Based Hair Removal System," Lasers. Surg. Med. Supp. 13:97 (2001).
Rosenfeld, H., et al., "Treatment of Cutaneous and Deep Vascular Lesions with the Nd:YAG Laser," Lasers in Surgery and Medicine, 6:20-23 (1986).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al., "Thermal Effects During Desensitisation of Teeth with Gallium-Aluminum-Arsenide Lasers," University of Queensland Dental School, Periodontology 15: 25-30 (1994).
Schade, W. et al., "Temperature tuned distributed feedback dye laser with high repetition rate", Applied Optics, vol. 29, No. 27, Sep. 20, 1990, pp. 3950-3954.
Schappert et al., "Temperture Tuning of an Organic Dye Laser" Applied Physics Letters 13(4):124-126 (Aug. 15, 1968).
Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Shimbashi, T. et al., "Ruby laser treatment of pigmented skin lesions," Aesth. Plast. Surg., vol. 19, pp. 225-229, 1995.
Shimizu et al., "Prospect of Relieving Pain Due to Tooth Movement During Orthodontic Treatment Utilizing a GA-AL As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Shuster, "Acne: The Ashes of a Burnt Out Controversy," Acta Derm. Venereol. Suppl. (Stockh), 120:43-46, 1985.
Sigurdsson et al., "Phototherapy of Acne Vulgaris with Visible Light," Dermatology, 194:256-260, 1997.
Sing, "Electroacupuncture and Laser Stimulation Treatment: Evaluation by Somatosensory Evoked Potential in Conscious Rabbits," Abstract AM-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops", http://www.usmedicine.com/articles/novel-use-of-fractional-lasers-for-sca-rring-improves-quality-of-life-for-injured-troops-.html, (Aug. 2012), U.S. Medicine ISSN: 0191-6246. 4 pages.
Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.
Strauss et al., "Skin Lipids and Acne," Annu. Rev. Med., 26:27-31, 1975.
Sumian, C.C. et al., "A Preliminary Clinical and Histopathological Study Of Laser Skin Resurfacing Using A frequency-Doubled Nd:YAG Laser After Application of Chromofilm.RTM.," Journal of Cutaneous Laser Therapy, vol. 1, pp. 159-166, 1999.
Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.
Sumian et al., "A new method to improve penetration depth of dyes into the follicular duct: . . . , " J. Am. Acad. Dermatol., 41(2) Part 1:172-175,1999.
Tarasov, L. V., Laser Physics, Translated from Russion by Ram S. Wadhwa, MIR publishers, Moscow, pp. 178-181, Chapter 2, 1983.
Tarijian, et al., "Fractional abalative laser skin resurfacing: A review", Journal of Cosmetic and Laser Therapy, 13:262-264, ISSN 1476/4172. Informa UK Ltd. Sep. 2011, 3 pages.
Taylor, C.R. et al., "Treatment of tattoos by Q-switched ruby laser," Arch. Dermatol, vol. 126, pp. 893-899, Jul. 1990.
Togatov, V.V. et al., "Discharge Circuit for Solid-State Lasers Pumping," Optical Journal, vol. 67, No. 4, pp. 92-96 (2000).
Tuchin, V.V., "Laser light scattering in biomedical diagnostics and therapy," Journal of Laser Applications, vol. 5, No. 2-3, pp. 43-60, 1993.
Unger, W.P., Laser hair transplantation III: Computer-assisted laser transplanting. Dermatol Surg. 1995;21:1047-1055.
Van Bruegel, "Power Density and Exposure Time of He—Ne Irradiation Are More Important Than Total Energy Dose in Photo-Biomodulation of Human Fibroblasts in Vitro," Lasers in Surgery and Medicine, vol. 12 pp. 528-537, 1992.
Vasily, et al., "Non-Ablative Fractional Resurfacing of Surgical and Post-Traumatic Scars", Journal of Drugs in Dermatology, 8(11):998-1005, Nov. 2009, 8 pages.
Walsh, "Laser "Curettage": a Critical Analysis," Periodontology 14:4-12, 1993.
Watanabe, S. et al., "Comparative studies of femtosecond to microsecond laser pulses on selective pigmented cell injury in skin," Photochemistry and Photobiology, vol. 53, No. 6, pp. 757-762, 1991.
Watanabe, S. et al., "The Effect of Pulse Duration on Selective Pigmented Cell Injury by Dye Lasers," The Journal of Investigative Dermatology, 88:523, 1987.
Watson, G. M., MS, "Minimally Invasive Therapies of the Prostate," Minimally Invasive Therapy, 1:231-240 (1992).
Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.
Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.
Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Wilson, S.W., "Passive Alignment of a Semiconductor Laser to an Optical Fiber," Universirty of Maryland, Masters Thesis (1995).
Winters, B.H. et al., "Photochemical Products in Coumarin Laser Dyes," Laboratory for Physical Sciences, College Park, MD, Aug. 26, 1974.
Yang et al., "Hybrid optoelectronics: A polymer laser pumped by a nitride light emitting diode," Applied Physics Letters 92, Jan. 23, 2008.
Yules, R.B. et al., "The effect of Q-switched ruby laser radiation on dermal tattoo pigment in man," Arch Surg, vol. 95, pp. 179-180, Aug. 1967.
Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.

(56) References Cited

OTHER PUBLICATIONS

Zonios et al., "Skin Melanin, Hemoglobin, and Light Scattering Properties can be Quantitatively Assessed in Vivo Using Diffuse Reflectance Spectroscopy," Journal of Investigative Dermatology, 117:1452-1457 (Dec. 2001).

Office Action dated Jul. 12, 2013 in U.S. Appl. No. 12/534,357 (10 pages).

Jacques, Steven L., "Role of Tissue Optics and Pulse Duration on Tissue Effects during High-Power Laser Irradiation" Applied Optics, May 1, 1993, pp. 2447-2454, vol. 32, No. 13, Optical Society of America.

Herd, Robert M. et al., "A Clinical and Histologic Prospective Controlled Comparative Study of the Picosecond Titanium: Sapphire (795 nm) Laser Versus the Q-switched Alexandrite (752 nm) Laser for Removing Tattoo Pigment" Journal of the American Academy of Dermatology, Apr. 1999, pp. 603-606, vol. 40, American Academy of Dermatology, Inc.

Ho, Darwin D.-M. et al.,"Laser-Tattoo Removal—A Study of the Mechanism and the Optimal Treatment Strategy via Computer Simulations" Lasers in Surgery and Medicine, 2002, pp. 389-397, vol. 30, Wiley-Liss, Inc.

Kilmer, Suzanne Linsmeier, et al.,"Picosecond and Femtosecond Laser Treatment of Tattoo Ink," Lasers in Surgery and Medicine, Sep. 8, 1996, pp. 36, No. 203, Wiley-Liss, Inc.

Ross, CDR E. Victor, et al.,"Comparison of Responses of Tattoos to Picosecond and Nanosecond Q-Switched Neodymium: YAG Lasers" Arch Dermatol, Feb. 1998, pp. 167-171, vol. 134, American Medical Association.

European Search Report (ESR) and Opinion EP Application No. 07811128.3, dated Sep. 28, 2016.

"Innovative Non-Surgical Treatment for Barrett's Esophagus", Jul. 1995, see http:/7wvvvv.plsaroup.com/da950728.htm.

Brauer, Jeremy A. et al., "Successful and Rapid Treatment of Blue and Green Tattoo Pigment With a Novel Picosecond Laser", Archives of Dermatology, vol. 148, No. 7, 2012, pp. 820-823.

Ertan et al., "Esophagel Adenocarcinoma Associated with Barrett's Esophagus: Long-term Management with Laser Ablation", Am. J. Gastro, 90: pp. 2201-2203, 1995.

Habbema, Louis et al., "Minimally invasive non-thermal laser technology using laser-induced optical breakdown fir skin rejuvenation", J. Biophotonics, vol. 5, No. 2, 2012, pp. 194-199.

Kliewer, Michael L. et al., "Excited State Absorption of Pump Radiation as a Loss Mechanism in Solid-State Lasers", IEEE Journal of Quantum Electronics, vol. 25, 1989, pp. 1850-1854.

Kuizenga, Dirk J. et al., "FM and AM Mode Locing of the Homogenous Laser—Part I: Theory", IEEE Journal of Quantum Electronics, vo. 6, No. 11, Nov. 1970, pp. 694-708.

Lee, Junsu et al., "Q-switched Mode-Locking of an Erbium-doped Fiber Laser through Subharmonic Cavity Modulation", Photonics Conference (IPC), 202 IEEE, Sep. 23, 2012, pp. 664665.

Mingxin, Qiu et al., "Performance of a Nd:YV04 microchip laser with continuous-wave pumping at wavelengths between 741 and 825 nm", Applied Optics, vol. 32, No. 12, Apr. 20, 1993, p. 2085.

Ogiso et al, "Phase Transitions of Rat Stratum Corneum Lipids By an Electron Paramagnetic Resonance Study and Relationship of Phase States to Drug Penetration," Biochimica et Biophysica Acta 1301:97-104 (1996).

Oraevsky, Alexander A. et al., "Plasma Mediated Ablation of Biological Tissues with Nanosecond-to-Femtosecond Laser Pulses: Relative Role of Linear and Nonlinear Absorption", IEEE Journal of Selected Topics in Quantum Electronics, vol. 2, No. 4, Dec. 1996, pp. 801-809.

Zayhowski, J.J. et al., "Gain-switched pulsed operation of microchip lasers", Optice Letters, Optical Society of America, US 14:23, Dec. 1, 1989, pp. 1318-1320.

Extended European Search Report & Written Opinion for EP 20155408, dated Apr. 17, 2020.

Goldman, L., Biomedical Aspects of the Laser, Springer-Verlag New York Inc., publishers, Chapts. 1, 2 & 23, 1967.

Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Grossman, M.C. et al., "Damage to hair follicles by normal-mode ruby laser pulses," Journal of he American Academy of Dermatology, vol. 35, No. 6, pp. 889-894, Dec. 1996.

Grossman, M.C. et al., "Laser Targeted at Hair Follicles," Lasers Med Surg., Suppl. 13:221 (2001).

Haedersal, et el., "Fractional Nonablative 1540 nm Laser Resurfacing for Thermal Burn Scars: a Randomized Controlled Trial", Lasers in Surgery and Medicine, 41:189-195, 2009, 7 pages.

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Johnsson et al., "No photoinactivation of Propionibacterium acnes with soft laser treatment," Dermatologica, 175(1):50, 1987.

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Kandel, Laurence B., M.D., et al., "Transurethral Laser Prostatectomy in the Canine Model," Lasers in Surgery and Medicine, 12:33-42 (1992).

Kantor et al., "Treatment of acne keloidalis nuchae with carbon dioxide laser," J. Am. Acad. Dermatol., 14:263-267, 1986.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," 8th Congress of International Society for Laser Surgery and Medicine, Mar. 30, 1987.

Kazmina et al., "Laser Prophlaxis and Treatment of Primary caries," SPIE vol. 1984, pp. 231-233.

Kilmer et al., "Pulse Dye Laser Treatment of Rhytids," American Society for Laser Medicine and Surgery Abstracts, p. 44 (Apr. 1997).

Klein E. et al., "Biological effects of laser radiation 1.," Northeast Electroncis Research and Engineering Meeting, NEREM Record, IEEE catalogue No. F-60, pp. 108-109, 1965.

Korobov et al., "Dependence of the Quantum Yield of Intercombinational Conversion into the Triplet State of Rhodamine 6G on the pH of the Medium", Zhur. Prikl. Spektrosk 24(1) (Jan. 28-31, 1976).

Kozlov et al., "Laser in Diagnostics and Treatment of Microcirculation Disorders Under Parodontitis," SPIE vol. 1984, pp. 253-264.

(56) References Cited

OTHER PUBLICATIONS

Krames et al. (2007) "Status and Future of High-Power Light-Emitting Diodes for Solid State Lighting," J. Display Technol., 3(2):160-175.
Kuhns J.G. et al., "Biological effects of laser radiation II Effects of laser irradiation on the skin," NEREM Record, pp. 152-153, 1965.
Kuhns J.G. et al., "Laser injury in skin," Laboratory Investigation, vol. 17, No. 1, pp. 1-13, Jul. 1967.
Leger, J. et al., "Geometrical Transformation of Linear Diode-Laser Arrays for Longitudinal Pumping of Solid-State Lasers," IEEE Journal of Quantum Electronics, vol. 28, No. 4, Apr. 1992.
Lesnik et al., "Agents that cause enlargement of sebaceous glands in hairless mice," Arch. Dermatol., 284:100-105, 1992.
Levin, G. et al., "Designing with hyseretic current-mode control," EDN Magazine, pp. 1-8, Apr. 11, 1996.
Levin, G. et al., "Designing with hyseretic current-mode control," EDN Magazine, pp. 1-8, Apr. 28, 1994.
Lucchina et al., "Fluorescence photography in the evaluation of acne," J. Am. Acad. Dermatol. 35:58-63 (1996).
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.
Manstein, D., et al., "Fractional Photothermolysis: A New Concept for Cutaneous Remodeling Using Microscopic Patterns of Thermal Injury," Lasers in Surgery and Medicine, 34: 426-438 (2004).
Manuskiatti et al., "Laser hair removal affects sebaceous glands and sebum excretion . . . ," J. Am. Acad. Dermatol., 41:176-180, 1999.
Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
Matsunaga et al., "Effect of pH on Dye-Laser Output Power", J. Appl. Phys. 48(2):842-844 (Feb. 1977).
Mccullough, David L., M.D., "Transurethral Laser Treatment of Benign Prostatic Hyperplasia," and "Transurethral Ultrasound-guided Laser-Induced Prostatectomy (TULIP) Procedure): A Canine Prostate Feasibility Study," by Roth, Robert A., M.D., et al., The Journal of Urology, 146:1126-1135(1991).
McDaniel, et al., "Hexascan: A New Robotized Scanning Laser Handpiece," Cutis, 45:300-305 (1990).
McNicholas, T. A., et al., "Interstitial Laser Coagulation of the Prostate: Experimental Studies," SPIE, 1421:30-35 (1991). (From Proceedings of Lasers in Urol., Laparoscopy, and General Surgery, Jan. 21-23, 1991).
Moretti, Michael, "Holmium Boosts Orthopedic Laser Development," Medical Laser Buyers Guide, p. 93 (1992).
Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. of Dermatol. Surg. 24:315-320 (1998).
Nemeth, et al., "Copper vapor laser treatment of pigmented lesions," Lasers Surg. Med. Supp. 2:51 (1990).
Altea Therapeutics, "The PassPort Patch makes medicines more effective and safer," www.alteatherapeutics.com, Sep. 30, 2004.
Altshuler, G. et al. "The ring resonator of optical quantum generator" Aug. 15, 1975. Invention description to certificate of authorship No. 719439.
Altshuler, G. et al. "The modulator of optical radiation intensity" Oct. 10, 1977. Invention description to ceilificate of authorship No. 741747.
Altshuler, G. et al. "Laser interferometric device to determine non-lineraity of an index of refraction of optical medium." Sep. 15, 1986. Invention description to certificate of authorship No. SU (11) 1257475 A1.
Altshuler, G. et al. "The way of determination of non-linerarity of an index of refraction of optical medium" Jul. 30, 1987. Invention description to certificate of authorship No. SU (11) 1326962 A1.
Altshuler, G. et al. "The way of investigation of radiation time structure of optical quantum generator." Jul. 9, 1974. Invention description to certificate of authorship No. 532304.
Mumford, Jaime, et al.,"Effect of Soft Laser Treatment on Wound Healing in the Hampster Oral Mucosa," Lasers in Surgery and Medicine, Supp. 8, Abstracts, Aug. 25, 1996.Biostimulation/Low Engergy Laser, pp. 5-8, American Society for Laser Medicine and Surgery Abstracts.
Walsh,L.J., "The current status of low level laser therapy in dentistry. Par 1. Soft tissue applications." Aust. Dent. J., Aug. 1997; 42(4): pp. 247-254. Department of Dentistry, University of Queensland.
U.S. Pat. No. 6,230,044, May 2001, Afanassieva et al. (withdrawn).
Zapka, et al., "Pulse Slicing and Pockels Cell Shutters," J. Phys. E: Sci, Instrum., vol. 15, 1982.
Russel, et al., "Flash-Lamp-Excited Self-Injection-Seeded Q-Switch Ti: Al2O3 Laser Oscillator," Applied Optics, vol. 35, No. 24, Aug. 20, 2996.
Ellenberger, et al., "Single-Frequency Nd:Glass Laser Oscillator with Pulse-Transmission-Mode Q-Switch," Optics Communications, vol. 81, No. 6, Mar. 15, 1991.
[No Author] Bioptron Light Therapy System. Website print-out, accessed Jul. 13, 2006 (2 pages).
[No Author] IPG Data Sheet for TFL Thulium Laser, Jun. 2001.
[No Author] Webpage www.gallery.com—RUTILE (Titanium Oxide)—Retrieved Oct. 3, 2011 from Http://www.galleries.com/minerals/oxides/rutile/rutile.htm. 2 pages.
[No Author] Energy Systems Coropration, "A Practical Guide for the PhotoDem.RTM.VL user," Haifa, Israel, Commercial Brochure 8 pages, Oct. 1995.
[No Author] "Final Report on the LFDL-10 Laser System for the GCA Corporation," Candela Corp., Natick, MA, Section II, subsection 5, pp. 13-15 & 27, Mar. 1982.
[No Author] "Fractional Photothermolysis Redefines Facial Skin Regeneration Science," Aesthetic Buyers Guide, Mar./Apr. 2004, www.miinews.com, pp. 1-4.
[No Author] "Hydrogel Dressings Contain Particles During Laser Therapy," Dermatology Times, ISSN-01966197, p. 26 (1994).
[No Author] "Instruction Manual, TFDL-10," Adapted for SLAC, Candela Corporation, Natick, Oct. 1985.
[No Author] "Lasers Battle for Prostatectomy Market," Medical Laser Industry Report, 5:1-3 (Aug. 1991).
[No Author] "LFDL-8 Instruction Manual," Candela Laser Corporation, Wayland, MA Revised Oct. 1987.
[No Author] "LFDL-8 Instruction Manual," Candela Laser Corporation, Wayland, MA, Jan. 1982, Revised Jun. 1987.
[No Author] "LFDL-8 Instruction Manual," Cynosure, Inc., Bedford, MA, Revised Nov. 1992.
[No Author] "Prostate Enlargement: Benigh Prostatic Hyperplasia," brochure from U.S. Department of Health and Human Services, pp. 1-14, (at least by 1992).
[No Author] "Special Instruction and Test Results for the LFDL-2 Wave Guide Laser," Candela Laser Corporation, Wayland, MA, Sep. 1982.
[No Author] "The Laser TURP Advantage," Intra-Sonix, Inc. pp. 1-4 (1991).
[No Author] Beckman Laser Institute "Experimental PDT to Prevent Esophegus Cancer," (8 pages) 1996.
[No Author] Cynosure Dioderm 510(k) Notification K992765 for Cynosure, Inc. to Food and Drug Administration, dated Aug. 16, 1999 and Aug. 20, 1999 (Additional Information).
[No Author] Reliant Technologies, Inc. "Physicians Guide: Understanding Fraxel Laser Treatment," pp. 1-10 (2004).

(56) References Cited

OTHER PUBLICATIONS

[No Author] Ritter Sybron Corporation, "Electrosurgery, A Guide for Operating Room Personnel," pp. 1-22, (Jun. 1976).
[No Author] Selective Photothermolysis of Sebaceous Glands, Department of Health and Human Services, Public Health Service, Small Business Innovation Research Program II Grant Application, Cynosure, Inc., dated: Jul. 27, 2000, pp. 17-39 and 43-44.
"American Society for Laser Medicine and Surgery Abstracts," Lasers in Surgery and Medicine, Supplement 6, p. 46 (1994).
Anderson, R.R., et al., "Microvasculature Can Be Selectively Damaged Using Dye Lasers: A Basic Theory and Experimental Evidence in Human Skin," Lasers in Surgery and Medicine 1:263-276 (1981).
Altshuler et al., "Human Tooth as an Optical Device," SPIE vol. 1429 Holography and Interferometry and Optical Pattern Recognition in Biomedicine, pp. 95-104, 1991.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Altshuler, et al., "Self Canalization of Laser Microbeam in Tissue as Fundamental Mechanism of Fractional Skin Resurfacing", Lasers in Surgery and Medicine Supple 15, 21, 2003.
Altshuler, G.B. et al., "Acoustic response of hard dental tissues to pulsed laser action," SPIE, vol. 2080, Dental Application of Lasers, pp. 97-103, 1993.
Altshuler, G.B. et al., "Extended theory of selective photothermolysis," Lasers in Surgery and Medicine, vol. 29, pp. 416-432, 2001.
Amy, R.L. et al., "Selective mitochondrial damage by a ruby laser microbeam: An electron microscopic study," Science, vol. 15, pp. 756-758, Nov. 1965.
Anderson, R.R. et al., "Selective photothermolysis: Precise microsurgery by selective absorption of pulsed radiation," Science, vol. 220, pp. 524-527, Apr. 1983.
Anderson, R.R. et al., "The optics of human skin," Journal of Investigative Dermatology, vol. 77, No. 1, pp. 13-19, 1981.
Angelis, et al., "Fractional, Non-Ablative Laser Therapy for the Treatment of Striae Distensae", White Paper published by Palomar Medical Technologies, Inc. (2009) 5 pages.
Mar. 2, 2022—(EP) Extended European Search Report—App. No. 21214044.6.
Bishop, A. I. and P. F. Barker "Subnanosecond Pockels cell switching using avalanche transistors." Review of scientific instruments 77.4: 044701 (2006).
Brauer, J. A., et al. "Use of a picosecond pulse duration laser with specialized optic for treatment of facial acne scarring." JAMA dermatology 151.3: 278-284 (2015).
Coyle, D. B., et al. "An interactive numerical model of diode-pumped, Q-switched/cavity-dumped lasers." Journal of Physics D: Applied Physics 28.3: 452 (1995).
Degnan, John J. "Theory of the optimally coupled Q-switched laser." IEEE Journal of Quantum Electronics 25.2: 214-220 (1989).
Fletcher, Aaron N. "FY 1980 Report on Dye Laser Materials" Naval Weapons Center China lake, California 93555. Feb. 1981.
Gerstman, B., et al. "Laser induced bubble formation in the retina." Lasers in Surgery and Medicine 18.1: 10-21 (1996).
Knipe et al. "Effects of Secondary Chemical Reactions Upon the performance of Dye Lasers" Journal of Photochemistry, 23 (1983) 117-130.
Mcdaniel, David. "Gene expression analysis in cultured human skin fibroblasts following exposure to a picosecond pulsed alexandrite laser and specially designed focus optic." Lasers in surgery and medicine 47:8 (2015).
Mirkov, M., et al. "Theoretical analysis of the mechanism producing the histologically observed epidermal changes with a picosecond alexandrite laser with diffractive lens array.", Lasers in Surgery and Medicine 48:1 (2016).
Nielsen, K. P., et al. "Retrieval of the physiological state of human skin from UV-Vis reflectance spectra—a feasibility study." Journal of Photochemistry and Photobiology B: Biology 93.1: 23-31 (2008).
Roth et al. "Transurethral Ultrasound-guided Laser-Induced Prostatectomy (TULIP) Procedure): A Canine Prostate Feasibility Study," The Journal of Urology, 146:1126-1135 (1991).
Scheps et al., "Alexandrite Laser Pumped by Semiconductor Lasers," Appl. Phys. Lett. 56(23), 2288-2290 (1990).
Shand, M., and H. Jenssen. "Temperature dependence of the excited-state absorption of alexandrite." IEEE Journal of Quantum Electronics 19.3: 480-484 (1983).
Siegman, "Lasers," University Science Books, 1986, Ch.25, p. 976.
Tanghetti, Emil. "Characterization of the histologic changes in the skin from treatment with a 755nm picosecond alexandrite laser with a fractional optic." Lasers in surgery and medicine 47:24 (2015).
Tanghetti, Emil. "The histology of skin treated with a picosecond alexandrite laser and a fractional lens array." Lasers in surgery and medicine 48.7: 646-652 (2016).
Thomas, G. M., et al. "Diode-pumped Alexandrite lasers in Q-switched and cavity-dumped Q-switched operation." Optics Express 24.24: 27212-27224 (2016).
Togatov, V.V. et al., "Electronic discharge module for pump systems of solid-state lasers", J. Opt/ Technol., vol. 67, No. 4, pp. 379-382 (2000).
Vogel, A., et al. "Shock wave emission and cavitation bubble generation by picosecond and nanosecond optical breakdown in water." The Journal of the Acoustical Society of America 100.1: 148-165 (1996).
Werner, S., et al. "Keratinocyte-fibroblast interactions in wound healing." Journal of investigative dermatology 127.5: 998-1008 (2007).
Apfelberg et al. "Analysis of Complications of Argon Laser Treatment for Port Wine Hemangiomas with Reference to Striped Technique," Lasers in Surgery and Medicine, 2:357-371 (1983).
Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Apfelberg, D.B., "A Preliminary Study of the Combined Effect of Neodymium:YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).
Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superselective Embolization," Lasers in Surgery and Medicine, 10:217-223 (1990).
Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.
Bjerring, P. et al., "Selective Non-Ablative Wrinkle Reduction by Laser," J Cutan Laser Ther, vol. 2, pp. 9-15, 2000.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida, vol. 42, pp. 7-23, 2011, 17 pages.
Bohm et al., "The Pilosebaceous Unit is Part of the Skin Immune System," Dermatology, 196:75-79, 1998.
Boiteux, M., et al., "A Transverse Flow Repetitive Dye Laser," Applied Optics, 9, 514 (1970).
Boulnois, J., "Photophysical Processes in Recent Medical Laser Developments: a Review," Lasers in Medical Science, vol. 1:47-66 (1986).
Britt et al., "The Effect of pH or Photobleaching of Organic Laser Dyes", IEEE J. Quantum Electron. (Dec. 1972), 913-914.

(56) References Cited

OTHER PUBLICATIONS

Burlamacchi et al., "A Simple Reliable Waveguide Dye Laser for Ophthalmological Applications," Rev of Sci Instrum; vol. 46; No. 3; pp. 281-283, Mar. 1975.

Chan, E.K., "Effects of Compression on Soft Tissue Optical Properties," IEEE Journal of Selected Topics in Quantum Electronics, vol. 2, No. 4, pp. 943-950 (Dec. 1996).

Costello, A. et al., "Nd:YAG Laser Ablation of the Prostate as a Treatment for Benign Prostatic Hypertrophy," Lasers in Surgery and Medicine, 12:121-124 (1992).

Cunliffe, "Acne Vulgaris. The Past, the Present and the Future," Acta Bermatovener (Stockh) Suppl. 120, pp. 34-38, 1985.

Dabrowska, "Intravital Treatment of the Pulp with Stimulation Laser Biostimulation," Abstract Rocz-Akad-Med-Bialymst. 1997; 42(1): 168-76.

Dierickx, C.C. et al., "Thermal Relaxation of Port-wine Stain Vessels Probed in Vivo: The Need for 1-10 Millisecond Laser Pulse Treatment," The Journal for Investigative Dermatology, pp. 709-714 (1995).

Dixon et al. "Hypertrophic Scarring in Argon Laser Treatment of Port-Wine Stains," Plastic and Reconstructive Surgery, 73:771-777 (1984).

Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).

Doukas et al., "Transdermal Drug Delivery With a Pressure Wave," Advanced Drug Delivery Reviews 56 (2004), pp. 559-579.

Dover J.S. et al., "Pigmented guinea pig skin irradiated with Q-switched ruby laser pulses," Arch Dermatol, vol. 125, pp. 43-49, Jan. 1989.

Dufresne et al., "Squamous cell carcinoma arising from the follicular occlusion triad," J. Am. Acad. Dermatol. 35(3), Part 1:475-477, 1996.

Fallon Friedlander, "Effective Treatment of Acne Fulminans-Associated Granulation Tissue with the Pulsed Dye Laser," Pediatric Dermatology, 15(5):396-398, 1998.

Finkelstein L.H. et al., "Epilation of hair-bearing urethral grafts using the neodymium:yag surgical laser," Journal of Urology, vol. 146, pp. 840-842, Sep. 1991.

Fiskerstrand E.J. et al., "Hair Removal with Long Pulsed Diode Lasers: A Comparison Between Two Systems with Different Pulse Structures," Lasers in Surgery and Medicine, vol. 32, pp. 399-404, 2003.

Forrest-Winchester et al., "The Effect of Infrared Laser Radiation on Dentinal Permeability in vitro," Department of Dentistry, University of Queensland Dental School, pp. 1-8, 1992.

Friedman-Binrbaum et al., "Seborrheic Skin and Acne Vulgaris as Protective Factors against the Development of Basal Cell Epithelioma," Dermatolgica, 183:160-163, 1991.

Furomoto, H., "Dye Chemisry and System Study for Optimum Laser Operation at 436 NM Using the LFDL-10 Laser," Prepared for Burlington Division Geophysical Corporation of America, pp. 1-23, Mar. 1982.

Ginsbach et al. "New Aspects in the Management of Benign Cutameous Tumors," Laser 79 Opto-Electronics, Munich Conference Proceedings, 344-347 (1979).

Goldberg, "Lasers for Facial Rejuvenation", Am J. Clin. Dermatol., 4(4):225-234, 2003, 10 pages.

Goldberg, "Nonablative Resurfacing", Clinics in Plastic Surgery, Skin Laser and Surgery Specialists of New York and New Jersey. Westwood, New Jersey. vol. 27, No. 2, Apr. 2000, 6 pages.

Goldman, L. et al., "Effect of the laser beam on the skin, HL Exposure of cytological preparations," Journal of Investigative Dermatology, vol. 42, pp. 247-251, 1964.

Goldman, L. et al., "Effect of the laser beam on the skin, Preliminary report" Journal of Investigative Dermatology, vol. 40, pp. 121-122, 1963.

Goldman, L. et al., "Impact of the laser on nevi and melanomas," Archives of Dermatology, vol. 90, pp. 71-75, Jul. 1964.

Goldman, L. et al., "Laser action at the cellular level," JAMA, vol. 198, No. 6, pp. 641-644, Nov. 1966.

Goldman, L. et al., "Laser treatment of tattoos, A preliminary survey of three year's clinical experience," JAMA, vol. 201, No. 11, pp. 841-844, Sep. 1967.

Goldman, L. et al., "Long-term laser exposure of a senile freckle," ArchEnviron Health, vol. 22, pp. 401-403, Mar. 1971.

Goldman, L. et al., "Pathology, Pathology of the effect of the laser beam on the skin," Nature, vol. 197, No. 4870, pp. 912-914, Mar. 1963.

Goldman, L. et al., "Preliminary investigation of fat embolization from pulsed ruby laser impacts of bone," Nature, vol. 221, pp. 361-363, Jan. 1969.

Goldman, L. et al., "Radiation from a Q-switched ruby laser, Effect of repeated impacts of power output of 10 megawatts on a tattoo of man," Journal of Investigative Dermatology, vol. 44, pp. 69-71, 1965.

Goldman, L. et al., "Replica microscopy and scanning electron microscopy of laser impacts on the skin," Journal of Investigative Dermatology, vol. 52, No. 1, pp. 18-24, 1969.

Goldman, L. et al., "The biomedical aspects of lasers," JAMA, vol. 188, No. 3, pp. 302-306, Apr. 1964.

Goldman, L. et al., "The effect of repeated exposures to laser beams," Acta derm.-vernereol., vol. 44, pp. 264-268, 1964.

Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

Goldman, L., "Effects of new laser systems on the skin," Arch Dermatol., vol. 108, pp. 385-390, Sep. 1973.

Goldman, L., "Laser surgery for skin cancer," New York State Journal of Medicine, pp. 1897-1900, Oct. 1977.

Goldman, L., "Surgery by laser for malignant melanoma," J. Dermatol. Surg. Oncol., vol. 5, No. 2, pp. 141-144, Feb. 1979.

Goldman, L., "The skin," Arch Environ Health, vol. 18, pp. 434-436, Mar. 1969.

Goldman, Leon, and Robert G. Wilson. "Treatment of basal cell epithelioma by laser radiation." Jama 189, No. 10 (1964): 773-775.

Aug. 28, 2008 (WO) International Search Report corresponding to PCT/US07/17536.

May 5, 2011 (EP) Examination Report relating to corresponding EP Application No. 07811128.3.

Apr. 28, 2010 (EP) Supplementary European Search Report relating to corresponding EP 07811128.

Dec. 5, 1978 (JP) English Abstract of JP 55077187.

Aug. 10, 2009 (WO) International Preliminary Reporton Patentability relating to corresponding PCT/US07/17536.

"American Society for Laser Medicine and Surgery Abstracts," Lasers in Surgery and Medicine, p. 51. Year 1990.

Goldman, M. P. (1995). "Sclerotherapy: Treatment of Varicose and Telangiectatic Leg Veins" Mosby, St.

Kelly, K., J. S. Nelson, T. E. Milner, G. Lask, P. Lee, M. Seyfzadeh, R. Geronemus et al. "Nonablative Laser Treatment of Facial Rhytides: United States Phase II Clinical Study." Lasers Surg Med 105 (1998): 38.

* cited by examiner

PICOSECOND LASER APPARATUS AND METHODS FOR ITS OPERATION AND USE

RELATED APPLICATION DATA

This application is a continuation application which claims priority to U.S. application Ser. No. 17/070,119, filed on Oct. 14, 2020, which is a divisional of U.S. patent application Ser. No. 14/708,828, filed on May 11, 2015, which is a continuation of U.S. patent application Ser. No. 12/534,379, filed on Aug. 3, 2009, which is a divisional of U.S. patent application Ser. No. 11/461,812, filed on Aug. 2, 2006, U.S. Pat. No. 7,586,957, issued on Sep. 8, 2009, each of which are hereby incorporated by reference in their entireties.

FIELD OF THE INVENTION

The present invention relates to apparatuses and methods for delivering laser energy having a short pulse duration (e.g., less than about 1 nanosecond) and high energy output per pulse (e.g., greater than about 250 millijoules). The desired operating parameters are achieved through the application of a bias voltage, having a time-dependent value as described herein, to an electro-optical device such as a Pockels cell. The Pockels cell may be disposed in a single laser having a resonator that can be operated in two modes, depending on the bias voltage applied to the electro-optical device. As a result, laser energy suitable for a number of applications, including treating and removing pigment particles such as those introduced to the human body as tattoos, may be generated using a relatively simple apparatus.

BACKGROUND OF THE INVENTION

Lasers are recognized as controllable sources of radiation that is relatively monochromatic and coherent (i.e., has little divergence). Laser energy is applied in an ever-increasing number of areas in diverse fields such as telecommunications, data storage and retrieval, entertainment, research, and many others. In the area of medicine, lasers have proven useful in surgical and cosmetic procedures where a precise beam of high energy radiation causes localized heating and ultimately the destruction of unwanted tissues. Such tissues include, for example, subretinal scar tissue that forms in age-related macular degeneration (AMD) or the constituents of ectatic blood vessels that constitute vascular lesions.

The principle of selective photothermolysis underlies many conventional medical laser therapies to treat diverse dermatological problems such as leg veins, portwine stain birthmarks, and other ectatic vascular and pigmented lesions. The dermal and epidermal layers containing the targeted structures are exposed to laser energy having a wavelength that is preferentially or selectively absorbed in these structures. This leads to localized heating to a temperature (e.g., to about 70° C.) that denatures constituent proteins or disperses pigment particles. The fluence, or energy per unit area, used to accomplish this denaturation or dispersion is generally based on the amount required to achieve the desired targeted tissue temperature, before a significant portion of the absorbed laser energy is lost to diffusion. The fluence must, however, be limited to avoid denaturing tissues surrounding the targeted area.

Fluence, however, is not the only consideration governing the suitability of laser energy for particular applications. The pulse duration and pulse intensity, for example, can impact the degree to which laser energy diffuses into surrounding tissues during the pulse and/or causes undesired, localized vaporization. In terms of the pulse duration of the laser energy used, conventional approaches have focused on maintaining this value below the thermal relaxation time of the targeted structures, in order to achieve optimum heating. For the small vessels contained in portwine stain birthmarks, for example, thermal relaxation times and hence the corresponding pulse durations of the treating radiation are often on the order of hundreds of microseconds to several milliseconds.

The use of even shorter pulses, however, results in a change from photothermal to photomechanical processes. The latter mechanism is invoked by applying laser pulses having a duration that is below the acoustic transit time of a sound wave through targeted particles. This causes pressure to build up in the particles, in a manner analogous to the accumulation of heat within a target irradiated by laser pulses having a duration that is below the thermal relaxation time.

Photomechanical processes described above can provide commercially significant opportunities, particularly in the area of treating skin pigmentations including tattoos, portwine stains, and other birthmarks. The incidence of tattoos in the U.S. and other populations, for example, continues at a significant pace. Because tattoo pigment particles of about 1 micron in diameter or less may be cleared from the body via ordinary immune system processes, stable tattoos are likely composed of pigment particles having diameters on the order of 1-10 microns or more. As the speed of sound in many solid media is approximately 3000 meters/second, the acoustic transit time across such particles, and consequently the laser pulse duration required to achieve their photomechanical destruction, is as low as hundreds of picoseconds. The acoustic transit time of a sound wave in a particle is calculated by dividing the radius of the particle by the speed of sound in the particle.

In addition to such short pulse durations, high energy laser pulses are needed for significant disruption of tattoo pigment particles and other pigmentations. Required fluences of several joules per square centimeter and treatment spot sizes of a few millimeters in diameter translate to a desired laser output with several hundred millijoules (mJ) per pulse or more. Unfortunately, current systems capable of such short pulse duration and high energy output are too complex and/or expensive for practical use in the treatment or removal of tattoos and other pigmentations. These devices generally require two or more lasers and amplifier stages, together with multiple electro-optical and/or acousto-optic devices.

Sierra and Russell (SBIR Proposal to the NIH, submitted December 1993) disclose a device of reduced complexity, which demonstrated 100 millijoules of output. The device uses a single laser gain medium that is common to two resonators. A Pockels cell is used to sequentially select one or the other of the two resonators. Operation requires applying a bias voltage to the Pockels cell to establish a modelocked pulse along the first resonator, switching the Pockels cell bias voltage to amplify the pulse along a second, separate resonator, and then switching the Pockels cell bias again to extract the amplified pulse. The gain or lasing medium, two polarizers, a Pockels cell, an acousto-optical device, and two mirrors are included along the optical pathway of the first resonator. The lasing medium, polarizers, electro-optical device, and an additional mirror are included along the optical pathway of the second resonator.

While this apparatus is less complex than multiple laser systems, it nevertheless requires a large number of optical components (e.g., seven or more). In addition, the voltages applied and switched at the Pockels cell are equal to the halfwave bias voltage of the Pockels cell, typically in excess of 5,000 volts. These voltages must be switched in less than a few nanoseconds, placing a significant demand on the switching electronics. Also, because the system utilizes the separate operation of two resonators, it is possible due to component limitations for radiation from one resonator to leak or "spill over" into another. A consequence of this is the generation of undesirable or "parasitic" pulses, particularly in the resonator used for amplification, which supports a significantly lower threshold for laser oscillation. Finally, the use of an acousto-optic modulator to achieve modelocking may require the constant adjustment of resonator length, as such devices operate only at discrete resonant frequencies.

The simpler alexandrite and other Q-switched lasers currently employed in the treatment of dermatological pigmentations cannot reliably achieve tattoo pigment particle clearance in a matter of only a few treatments, despite claims to the contrary. Consequently, there is a need in the art for laser apparatuses of relatively low complexity, such that they are practical for tattoo pigment particle removal and the treatment of other pigmented lesions. Such apparatuses, however, must also be capable of emitting laser radiation with the short pulse duration required to invoke photomechanical processes. As discussed above, this requires pulse durations on the order of several hundred picoseconds, or the acoustic transit time across targeted pigment particles. Also characteristic of such a device is the capability of achieving an output energy of several hundred millijoules or more.

BRIEF SUMMARY OF THE INVENTION

The present invention is associated with the discovery of methods and apparatuses described herein for delivering pulsed laser energy with pulse characteristics suitable for a number of practical applications. Such pulse characteristics include a sufficiently short duration and/or a sufficiently high energy for the photomechanical treatment of skin pigmentations and pigmented lesions, both naturally-occurring (e.g., birthmarks), as well as artificial (e.g., tattoos). Advantageously, rather than requiring at least two resonators (or laser cavities), pulsed laser energy having the desired characteristics may be generated, according to a particular embodiment of the present invention, with an apparatus having a single resonator and lasing (or gain) medium, together with an electro-optical device to effect switching between two different operating modes of the single resonator.

In addition to requiring only a single resonator and lasing (or gain) medium, apparatuses may be further simplified in that, in a first operating mode, a modelocked pulse is established in the resonator, without the use of an additional modelocking device such as an acousto-optic modulator. Moreover, the need to adjust resonator length, associated with the use of some acousto-optical devices, is eliminated. The overall component and operating requirements of apparatuses according to embodiments of the present invention are therefore considerably simplified. For example, in some cases only four optical components may be required, as is common in many Q-Switched laser systems.

These and other advantages are associated with the application, to an electro-optical device (e.g., a Pockels cell) positioned along the optical axis of the resonator, a time-dependent bias voltage having a periodic waveform with an amplitude to effect a first operating mode. In particular, the periodic waveform has a period substantially equal to the round trip time of laser energy oscillating in the resonator, which results in the generation of a modelocked pulse. Other aspects of the present invention include the electronics necessary to generate the time-dependent bias voltage described above, as well as optionally a baseline operating voltage and voltages for (A) implementing a second operating mode of the resonator which amplifies laser energy oscillating in the resonator and (B) thereafter extracting the amplified laser pulse, having the desired pulse duration and pulse energy characteristics.

In one embodiment, therefore, the present invention is a method for generating pulsed laser energy. The method comprises reflecting laser energy between two substantially totally reflective mirrors disposed at opposite ends of a resonator and through a polarizer and an electo-optical device within the resonator and positioned along the optical path (or longitudinal axis) of the resonator. A lasing (or gain) medium, for example a flashlamp pumped laser rod, is also positioned along the optical axis. The method further comprises applying to the electro-optical device a time-dependent bias voltage, $V(t)$, equal to the sum of a baseline voltage, $V_o$, and a time-dependent differential voltage, $\delta V(t)$. This time-dependent differential voltage varies periodically with a period substantially equal to twice the time required (i.e., the round trip time) for the laser energy to traverse the length of the resonator, allowing for operation in some cases without the need to make adjustments to the resonator length. The method may also involve setting or adjusting the amplitude of the time dependent differential voltage and/or pumping the lasing medium (e.g., using optical pumping means such as a flashlamp) under conditions sufficient to establish a modelocked pulse in the resonator. This provides a first mode of operation in the resonator.

In a subsequent, second mode of operation, the modelocked pulse is amplified. In the case where the electro-optical device is positioned between the polarizer and one of the mirrors (arbitrarily denoted the "second" mirror) a first (constant) bias voltage may be applied to the electro-optical device such that a pulse reflected at this second mirror traverses the polarizer substantially without loss of intensity or amplitude. To extract the energy from the amplified pulse, a second (constant) bias voltage may thereafter be applied to the electro-optical device such that the polarizer substantially expels a pulse reflected at the second mirror from the resonator. This releases the pulsed laser energy having the desired characteristics described herein.

The first bias voltage, for example, may be substantially 0 and the second bias voltage may be substantially equal to the quarter wave voltage of the electro-optical device. The baseline voltage, $V_o$, is generally from about 30% to about 70%, and often from about 40% to about 60%, of the quarter wave voltage of the electro-optical device. The time-dependent differential voltage, $\delta V(t)$, has an amplitude generally from about 5% to about 35%, and often from about 10% to about 30%, of the quarter wave voltage of the electro-optical device (e.g., Pockels cell). Advantageously, these voltages are one half or less than the halfwave voltage (required in known methods) and therefore result in a significant reduction in the switching electronics requirements.

The pulsed laser energy generated according to methods of the present invention may have at least about 100 mj/pulse, and often will have from about 200 to about 800 mj/pulse, as required for applications described herein, such as the removal or dispersion of pigment particles as often used to form tattoos. As is also desired in these applications, the pulsed laser energy generally has a pulse duration of at most about 500 picoseconds (ps), typically at most about 300 ps, and often at most about 150 ps. As stated previously, any of the methods described above may be performed without the need to adjust resonator length.

Other embodiments of the invention include laser apparatuses for performing any of the methods described above, and in particular for generating pulsed laser energy with pulses having a duration of at most about 500 ps and an energy or intensity of at least about 100 mj. A representative apparatus comprises a resonator having first and second mirrors, each of which is substantially totally reflective, disposed at opposite ends of the resonator. The apparatus also includes a lasing material (e.g., a solid state lasing medium), an electro-optical device (e.g., a Pockels cell), and a polarizer, all of which are positioned along the optical axis of the resonator. The electro-optical device is positioned on this axis between the polarizer and the (arbitrarily denoted) "second" mirror.

The bias voltage of the electro-optical device may be modified such that two operating modes, pulse modelocking and pulse amplification, are carried out sequentially, as described above, in a single resonator. Therefore, apparatuses according to some embodiments of the invention do not include a modelocking device such as an acousto-optic modulator. In other embodiments, the apparatuses may include a resonator, and often include a single resonator only, which is configured to generate laser radiation with the desirable pulse duration and energy characteristics as discussed herein. The resonator may be included in the apparatus, for example, in the absence of any other components that would materially affect its basic and novel characteristics.

An additional aspect of the present invention involves the use of voltage waveform generating electronics for applying the necessary voltage during operation to the electro-optical device, in order to invoke the separate and normally sequential operating modes of the apparatus, as described above. In particular embodiments, these waveform generating electronics apply a time-dependent bias voltage, $V(t)$, equal to the sum of a baseline voltage, $V_o$, and a time-dependent differential voltage, $\delta V(t)$. The time-dependent differential voltage varies periodically with a period substantially equal to the round trip time required for the laser energy in the resonator.

The voltage waveform electronics may be used for initially applying the baseline voltage, $V_o$, to the electro-optical device, prior to applying the time-dependent differential voltage, $\delta V(t)$, which establishes a first, modelocked operating mode, as discussed above. Subsequently, the voltage waveform electronics can apply a first (constant) bias voltage (e.g., zero voltage or complete discharge of the electro-optical device), such that a reflected pulse at the second mirror traverses the polarizer substantially without loss of intensity. Under these conditions the lasing or gain medium amplifies the laser energy within the resonator, in a second, amplification operating mode, prior to its extraction or release from the apparatus as laser energy having the desirable pulse characteristics, including the short pulse duration and high pulse energy discussed above. This generation of such laser energy, for applications discussed herein, is ultimately effected by applying a second bias voltage (e.g., the quarter wave voltage) to the electro-optical device, such that a pulse reflected at the second mirror is substantially expelled from the resonator at the polarizer.

In embodiments of the invention, suitable voltage waveform generating electronics may include five switches (e.g., MOSFET switching transistors S1, S2, S3, S4, and S5, such as those depicted in the representative circuit diagram shown in FIG. 4) capable of modulating the voltage applied to the electro-optical device in a time frame on the order of 10 nanoseconds. Two high speed diodes and three voltage sources may be used in conjunction with these switches. A first voltage source, for example, may have the capability of applying the baseline voltage, $V_o$ (e.g., from about 30% to about 70% of the quarter wave voltage), to the electro-optical device upon closing S1 and S2 and opening S3, S4, and S5. A second voltage source may have the capability of periodically applying the time-dependent differential voltage $\delta V(t)$ (e.g., having a magnitude from about 5% to about 35% of the quarter wave voltage), such that the total bias voltage, $V(t)$, applied to the electro-optical device is $V_o+\delta V(t)$. This may be accomplished by closing S1 and opening S4 and S5, while periodically opening and closing S2 and S3 with a period substantially equal to the round trip time of the laser energy, in order to establish the first modelocked pulse operating mode.

Thereafter, the electro-optical device may be discharged by closing S3 and S5 and opening S1, S2, changing the value of the effective reflectivity, $R_{eff}$, of the second mirror to substantially 100%. This amplifies the laser energy within the resonator, in a second, amplification operating mode. Extraction or release of the desired laser energy from the apparatus may be achieved upon closing S1 and S4 while opening S2, S3, and S5, thereby applying, to the electro-optical device, the voltage differential between two of the three voltage devices, which is substantially equal to the quarter wave voltage of the device. This applied voltage in turn changes the value of $R_{eff}$ to substantially 0%.

In another embodiment, the present invention is a method for treating a skin pigmentation, such as a tattoo, a portwine stain, or a birthmark. The method comprises exposing pigmented skin of a patient to pulsed laser energy with pulses having a duration of at most about 500 ps and an energy of at least about 100 mj. The pulsed laser energy is generated according to any of the methods, or using any of the apparatuses, discussed above.

In another embodiment, the present invention is a method for removing a tattoo comprising tattoo pigment particles, which may, for example, have a diameter from about 1 to about 10 microns. The method comprises exposing the tattoo pigment particles to pulsed laser energy with pulses having a duration below about twice the acoustic transit time across the tattoo pigment particles. This pulsed laser energy may have pulses with a duration and energy as described above, and/or may be generated according to any of the methods, or using any of the apparatuses, discussed above.

These and other embodiments are apparent from the following Detailed Description.

Figure 2:
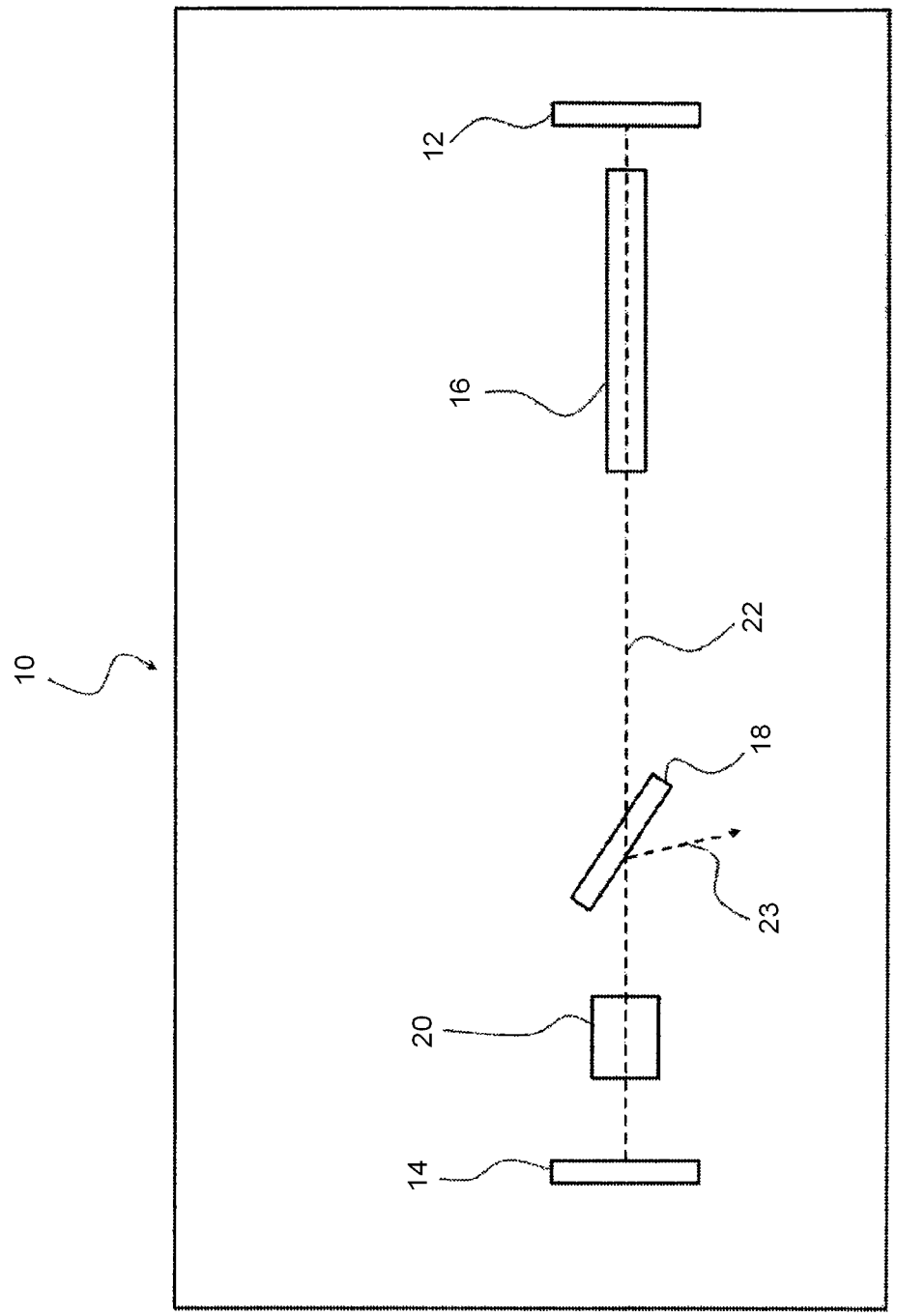
FIG. 2 depicts a representation of a laser emitting apparatus according to the present invention.

The features of the apparatus referred to in the above FIG. 2 are not necessarily drawn to scale and should be understood to present an illustration of the invention and/or principles involved. Some features depicted in the figures have been enlarged or distorted relative to others, in order to facilitate explanation and understanding. The same reference numbers are used in the figures for similar or identical components or features shown in the various embodiments. Laser devices, as disclosed herein, will have configurations, components, and operating parameters determined, in part, by the intended application and also the environment in which they are used.

DETAILED DESCRIPTION OF THE INVENTION

Aspects of the present invention are associated with the ability of laser pulses having a duration of several hundred picoseconds to cause the photomechanical disruption, through the use of sound (or pressure) waves, of tattoo pigment particles and other components of pigmented lesions. Mechanical disruption of the pigment particles facilitates removal of the pigment particles by the body's natural removal processes such as those associated with the immune system. These pulse durations are of the same order as the acoustic transit time across particles having a diameter from about 1 to about 10 microns, which are otherwise sufficiently large to remain stable in skin tissue (e.g., without being cleared by normal immune system responses).

Figure 1:
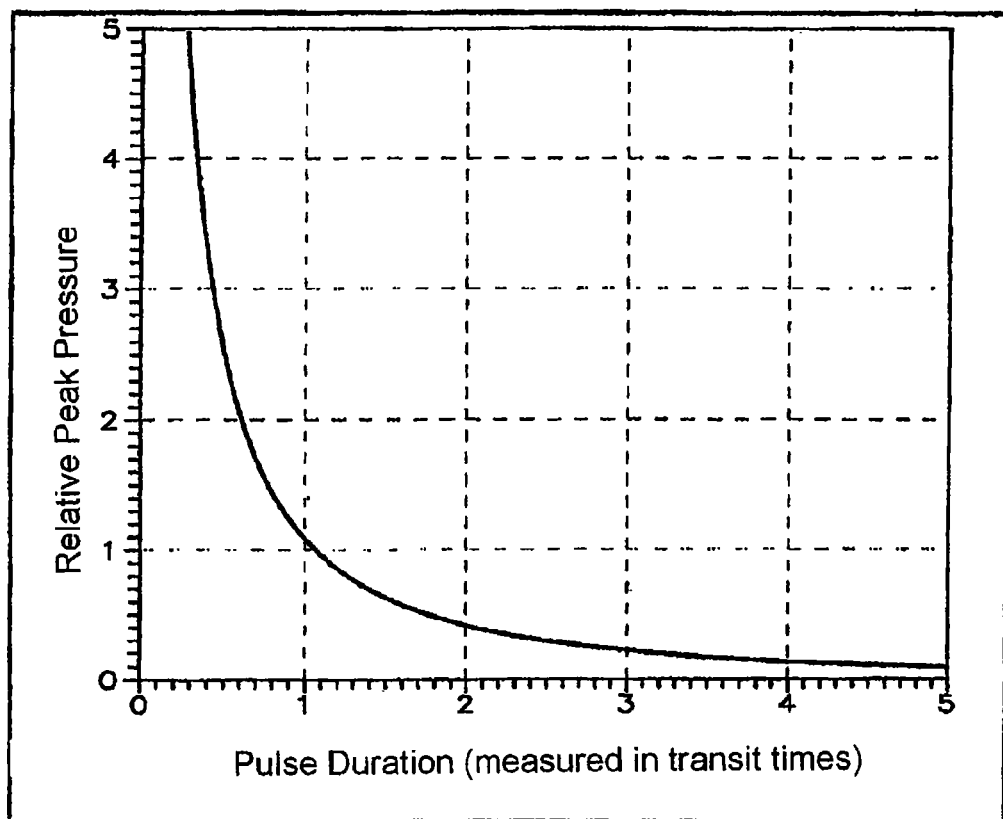
FIG. 1 is a graphical representation showing the relationship between the relative peak pressure within a particle targeted for photomechanical disruption, as a function of pulse duration, measured as a multiple of the acoustic transit time across the particle.

The significance of short pulse duration in photomechanical processes is illustrated graphically in FIG. 1, which shows the non-linear response of peak pressure in a target, as laser pulse duration is reduced. The units of pulse duration, along the x-axis, are normalized to a multiple of the acoustic transit time across a targeted particle, such as a tattoo pigment particle. The acoustic transit time refers to the time required for a sound wave to traverse this target particle. As is apparent from FIG. 1, the photomechanical stress on the target rapidly increases when the irradiating pulse duration decreases to less than about two transit times. The effect becomes dramatically more pronounced below about one transit time. FIG. 1 therefore illustrates the importance of the ability to operate in the picosecond pulse duration range, in designing a photomechanical treatment or removal protocol for tattoos and other pigmented skin lesions. In fact, as is also clear from FIG. 1, laser pulses having durations of greater than about five times the acoustic transit time induce relatively insignificant peak pressure on the target particle and are therefore relatively ineffective in disrupting small pigmentation particles via the photomechanical mechanism.

Effective apparatuses and methods according to embodiments of the present invention are therefore advantageously capable of delivering laser energy having a pulse duration generally less than about 1 nanosecond, typically less than about 500 picoseconds (ps), and often less than about 250 ps. Common pulse duration values according to some embodiments are in the range from about 100 to about 300 ps. The above values generally represent less than several (e.g., from about one to about three) acoustic transit times for pigmentation particles having a diameter in the range from about 1 to about 10 microns.

Also characteristic of laser energy that is effective for treating or removing skin pigmentations is a relatively high level of energy output. For example, fluences required to achieve significant disruption of pigment particles are generally in the range from about 1 to about 10 $j/cm^2$. For viable treatment methods having a treatment area or spot size of a few millimeters in diameter, the required laser output is preferably at least about 100 mj per pulse, and often in the range from about 200 to about 800 mj per pulse.

FIG. 2 depicts a representative embodiment of an apparatus 10 according to the present invention, which is capable of achieving the above pulse duration and energy output parameters, suitable for the effective treatment of pigmented lesions through photomechanical means. Advantageously, the apparatus includes a resonator (or laser cavity) capable of generating laser energy having the desirable pulse duration and energy per pulse, as described herein. The resonator has a characteristic longitudinal or optical axis 22 (i.e., the longitudinal flow path for radiation in the resonator), as indicated by the dashed line. Also included in the representative apparatus shown are an electro-optical device, in this case a Pockels cell 20, and a polarizer 18 (e.g., a thin-film polarizer). During operation, the laser pulse output will be obtained along output path 23.

At opposite ends of the optical axis 22 of the resonator are a first mirror 12 and a second mirror 14 having substantially complete reflectivity. This term, and equivalent terms such as "substantially totally reflective" are used to indicate that the mirrors 12 and 14 completely reflect incident laser radiation of the type normally present during operation of the resonator, or reflect at least 90%, preferably at least 95%, and more preferably at least 99% of incident radiation. The mirror reflectivity is to be distinguished from the term "effective reflectivity," which is not a property of the mirror itself but instead refers to the effective behavior of the combination of second mirror 14, Pockels cell 20, and polarizer 18 that is induced by the particular operation of the Pockels cell 20, as discussed in detail below.

In particular, a laser pulse traveling from lasing or gain medium 16 towards second mirror 14 will first pass through polarizer 18, then Pockels cell 20, reflect at second mirror 14, traverse Pockels cell 20 a second time, and finally pass through polarizer 18 a second time before returning to gain medium 16. Depending upon the bias voltage applied to Pockels cell 20, some portion (or rejected fraction) of the energy in the pulse will be rejected at polarizer 18 and exit the resonator along output path 23. The remaining portion (or non-rejected fraction) of the energy (from 0% to 100% of the energy in the initial laser pulse) that returns to the medium 16 is the "effective reflectivity" of second mirror 14. As explained above, for any given applied voltage to Pockels cell 20, the effective behavior of the combination of second mirror 14, Pockels cell 20, and polarizer 18 is indistinguishable, in terms of laser dynamics, from that of a single partially reflective mirror, reflecting the same non-rejected fraction described above. An "effective reflectivity of substantially 100%" refers to a mirror that acts as a substantially totally reflective mirror as defined above.

Also positioned along the optical axis 22 of the resonator is a lasing or gain medium 16, which may be pumped by any conventional pumping device (not shown) such as an optical pumping device (e.g., a flashlamp) or possibly an electrical or injection pumping device. A solid state lasing medium and optical pumping device are preferred for use in the present invention. Representative solid state lasers operate with an alexandrite or a titanium doped sapphire (TIS) crystal. Alternative solid lasing media include a yttrium-aluminum garnet crystal, doped with neodymium (Nd:YAG laser). Similarly, neodymium may be used as a dopant of pervoskite crystal (Nd:YAP or Nd:YAlO$_3$ laser) or a yttrium-lithium-fluoride crystal (Nd:YAF laser). Other rare earth and transition metal ion dopants (e.g., erbium, chromium, and titanium) and other crystal and glass media hosts (e.g., vanadite crystals such as YVO$_4$, fluoride glasses such as ZBLN, silicaglasses, and other minerals such as ruby) of these dopants may be used as lasing media.

The above mentioned types of lasers generally emit radiation, in predominant operating modes, having wavelengths in the visible to infrared region of the electromagnetic spectrum. In an Nd:YAG laser, for example, population inversion of Nd$^{+3}$ ions in the YAG crystal causes the emission of a radiation beam at 1064 nm as well as a number of other near infrared wavelengths. It is also possible to use, in addition to the treating radiation, a low power beam of visible laser light as a guide or alignment tool. Alternative types of lasers include those containing gas, dye, or other lasing media. Semiconductor or diode lasers also represent possible sources of laser energy, available in varying wavelengths. In cases where a particular type of laser emits radiation at both desired and undesired wavelengths, the use of filters, reflectors, and/or other optical components can aid in targeting a pigmented lesion component with only the desired type of radiation.

Aspects of the invention also relate to the manner in which the relatively simple apparatus 10, depicted in FIG. 2, is operated to generate laser energy with the desirable pulse duration and energy output requirements discussed above. For example, laser energy from the lasing medium 16 is reflected between the first mirror 12 and second mirror 14 at opposite ends of the optical axis 22 of the resonator. Laser energy emanating from the lasing medium 16 therefore traverses the thin film polarizer 18 and Pockels cell 20 before being reflected by the substantially totally reflective second mirror 14, back through the Pockels cell 20 and polarizer 18.

TIS materials, alexandrite, and other crystals such as Nd:YVO$_4$ exhibit a large stimulated emission cross-section selectively for radiation having an electric field vector that is aligned with a crystal axis. Radiation emitted from such lasing materials is therefore initially linearly polarized, requiring that the polarizer 18 be configured for transmission of essentially all incident radiation by proper alignment with respect to the electric field vector. However, the application of a bias voltage to the Pockels cell 20 can cause elliptical polarization of the exiting radiation, such that the radiation field of the pulse reflected in the second mirror 14 and arriving again at the polarizer 18 will in this case consist of two components with orthogonal electric field vectors being out of phase by some angle.

If the polarizer 18 rejects radiation having an electric field vector that is orthogonal (or perpendicular) to the orientation of the initial electric field vector of radiation from the lasing material 16, the net effect of the combined components (second mirror 14, Pockels cell 20, and polarizer 18) is that of a variable reflectivity mirror. The effective reflectivity, R$_{eff}$, of the second mirror 14 (i.e., the Pockels cell 20 being positioned between that mirror 14 and the polarizer 18), is given by equation (1):

$$R_{eff} = \cos^2\left(\frac{\Pi}{2} V/V_{\lambda/4}\right), \quad (1)$$

where the quantity V$_{\lambda/4}$ is the quarter wave voltage of the Pockels cell 20. The quarter wave voltage refers to the voltage required across the Pockels cell to split the incident radiation into two components having equal intensities and retard the polarization electrical field vector of one component by one-quarter of a wavelength relative to the other component.

Thus radiation, having been reflected at the second mirror 14 and therefore passing twice through the Pockels cell 20 with an applied voltage of V$_{\lambda/4}$, will have its polarization axis rotated 90° and will be completely rejected by polarizer 18. An applied voltage V=V$_{\lambda/4}$ therefore provides an effective reflectivity, R$_{eff}$, of "substantially 0%," meaning that the radiation is either completely rejected by the polarizer 18, or possibly all but a small amount of radiation is rejected (e.g., an amount having an intensity or amplitude generally of less than about 10%, typically of less than about 5%, and often less than about 1%, of its initial intensity or amplitude, I$_o$, prior to the first pass of the radiation through the polarizer 18 and Pockels cell 20). Overall, radiation arriving at the lasing medium 16 after two passes through Pockels cell 20 (and after having been reflected in the second mirror 14) will have an intensity or amplitude, I, given by $$I = I_o \cdot R_{eff}$$

It is recognized that, in various embodiments of the invention, the quarter wave voltage can actually induce a number of possible changes in incident radiation polarization, depending on the particular optical configuration of the apparatus. For example, the use of quarter wave retardation plate positioned between Pockels cell 20 and the second mirror 14 would introduce a double pass polarization axis rotation of 90°, without any applied voltage to the Pockels cell. The effective reflectivity, R$_{eff}$, of the second mirror 14 in this case would be governed by the expression $$R_{eff} = \cos^2\left[\frac{\Pi}{2}(V + V_{\lambda/4})/V_{\lambda/4}\right],$$

where a Pockels cell voltage of 0 would achieve an effective reflectivity of 0%. Application of the quarter wave voltage to the Pockels cell would then introduce an additional 90° of rotation, such that the overall effect would be that of no change in polarization. The effective reflectivity, R$_{eff}$, in this case would be substantially 100%, meaning that the second mirror 14 would act as a substantially totally reflective mirror. It is also recognized that not all lasing media emit linearly polarized radiation or radiation having an electric field vector that is aligned with a crystal axis. For example, Nd:YAG media are non-polarizing. In the case where non-polarizing media are employed, polarizer 18 may establish a given polarization of radiation incident to Pockels cell 20.

Various aspects of the present invention are associated with the advantages obtained when a time-dependent bias voltage, V(t), is applied to an electro-optical device such as the Pockels cell 20. In preferred embodiments of the invention, the time-dependent voltage is equal to the sum of a baseline voltage, V$_o$, and a time-dependent differential or offsetting voltage, δV(t), that varies periodically with a period substantially equal to the round trip time, or twice the time required for the oscillating laser energy to traverse the length of the resonator. The term "substantially equal" in this case refers to deviations between the period of the applied voltage waveform and the round trip time of generally less than about 100 parts per million (ppm), often less than 10 ppm, and preferably less than about 1 ppm.

The application of a time-dependent voltage waveform described above and characterized by equation (2)

$$V(t) = V_o + \delta V(t), \quad (2)$$

where the time-dependent component $\delta V(t)$ has a period substantially equal to the round trip time of the resonator, allows the resonator to function in a first operating mode, where a modelocked pulse is established in the resonator. Importantly, modelocked oscillation may be obtained without the requirement for an additional modelocking device (or modelocker), such as an acousto-optic modulator, and consequently without the need to adjust resonator length to match a particular resonance frequency.

Thus, the combination of components, together with the applied voltage waveform discussed above, can function essentially identically to a modelocker. In the first modelocked pulse operating mode, the effective reflectivity, $R_{eff}$, of the second mirror 14, is modulated, by modulating the voltage applied to the Pockels cell 20, with a desired frequency (corresponding to a period substantially equal to the round trip time of the oscillating laser energy). The modulated reflectivity over time $R(t)$ is obtained by substituting $V_o + \delta V(t)$ from equation (2) into the expression for $R_{eff}$ in equation (1) and expanding to obtain $$R(t) = R_o - 2\cos\left(\frac{\Pi}{2} V_o/V_{\lambda/4}\right)\sin\left(\frac{\Pi}{2} V_o/V_{\lambda/4}\right)$$
$$\left(\frac{\Pi}{2}\delta V(t)/V_{\lambda/4}\right) + \left[\sin^2\left(\frac{\Pi}{2}V_o/V_{\lambda/4}\right) - \cos^2\left(\frac{\Pi}{2}V_o/V_{\lambda/4}\right)\right]\left(\frac{\Pi}{2}\delta V(t)/V_{\lambda/4}\right)^2,$$

where $R_o$ is the initial effective reflectivity of the second mirror 14. From the above expression, it is evident that when operating at $V_o = V_{\lambda/4}$ or $V_o = 0$, the linear term vanishes and modulation of the reflectivity is consequently very small. In contrast, the maximum extent or degree of modulation occurs when the baseline voltage $V_o$ is 50% of the quarter wave voltage ($V_o = 0.5 V_{\lambda/4}$). In preferred embodiments, the baseline voltage $V_o$ is from about 30% to about 70%, and typically from about 40% to about 60%, of the quarter wave voltage of the Pockels cell.

Also, from the above equation for $R(t)$, approximately 30% modulation of the reflectivity can be achieved when the magnitude of $\delta V(t)$, representing either a positive or a negative deviation from $V_o$, is 20% of the quarter wave voltage. In other embodiments, the time-dependent differential voltage, $\delta V(t)$, has an amplitude generally from about 5% to about 35%, and typically from about 10% to about 30%, of the quarter wave voltage of the electro-optical device (e.g., the Pockels cell 20). Operation under these parameters, in a first modelocked pulse mode of operation, can therefore mimic the operation of a resonator having an 80% reflecting mirror at one end and also containing a modelocking device such as an acousto-optic device. Modelocking in either case requires a pumping system or device such as a flashlamp (not shown) operating with a sufficient pump rate to the lasing medium 16 to establish the modelocked pulse in the resonator.

In a second (amplification) mode of operation, subsequent to modelocking, the modelocked pulse generated as described above is amplified. Amplification is achieved by applying a constant (first) bias voltage to the Pockels cell 20 such that the second mirror 14 has an effective reflectivity of substantially 100%. In this condition, the modelocked pulse oscillates between two substantially totally reflective mirrors 12 and 14. In embodiments where the effective reflectivity $R_{eff}$ of the second mirror 14 is governed by equation (1) above, a first bias voltage of substantially 0 volts (or substantially complete discharge of the Pockels cell), will provide the desired reflectivity of substantially 100%. In this amplification mode, the laser energy can rapidly increase in amplitude by extracting energy that was previously pumped and stored in the lasing medium 16 during modelocking.

Once the laser energy, oscillating in the resonator under amplification conditions, has reached a desired or maximum amplitude, it can thereafter be extracted. This is achieved by applying a second bias voltage to the Pockels cell 20 such that the second mirror has an effective reflectivity $R_{eff}$ of substantially 0%, to generate pulsed laser energy. In embodiments where the effective reflectivity, $R_{eff}$, of the second mirror 14 is governed by equation (1) above, a second bias voltage equal to the quarter wave voltage of the Pockels cell will achieve the desired reflectivity of substantially 100%. At this point, laser radiation having the desirable pulse duration and energy output described herein, is generated from the apparatus 10 and exits the resonator along output path 23.

Figure 3A:
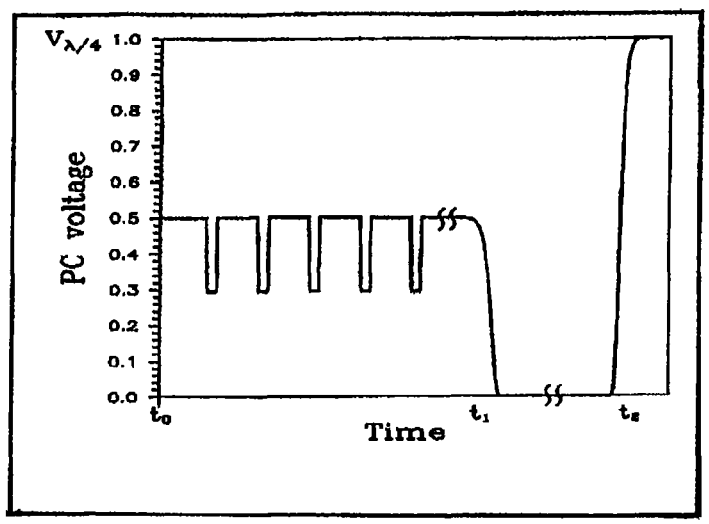
FIG. 3A is a graphical representation of voltage applied over time to an electro-optical device in a laser apparatus, corresponding to a value $V(t)=V_o+\delta V(t)$ between $t_0$ and $t_1$, a value $V(t)=0$ between $t_1$ and $t_2$, and a value $V(t)$ of the quarter wave voltage of the electro-optical device, after $t_2$.

FIG. 3A provides a representation of voltage applied, as a function of time, to an electro-optical device such as a Pockels cell in a laser apparatus, to achieve the operating modes described above. In the time period between $t_0$ and $t_1$, the voltage applied is according to the equation $V(t) = V_o + \delta V(t)$, with the time-dependent differential voltage, $\delta V(t)$, periodically offsetting an applied baseline voltage, $V_o$. In the particular embodiment of the invention using the voltage waveform shown in FIG. 3A, the baseline voltage is 50% of the Pockels cell quarter wave voltage ($V_o = 0.5 V_{\lambda/4}$) and the magnitude of the offset is 20% of the Pockels cell quarter wave voltage. This offset occurs periodically with a period equal to the round trip time of laser energy in the resonator.

During operation from time $t_0$ to $t_1$, the pump rate to the gain or lasing medium may be set or adjusted to exceed the threshold for laser oscillation, when $R_{eff}$ (the effective reflectivity of the second mirror) is at or near its highest value. Under these operating conditions, together with the condition that the period of the applied voltage waveform is substantially the round trip time for energy to traverse the resonator as described above, a modelocked pulse can be established within the resonator. The time period between $t_0$ and $t_1$, where a periodic voltage is applied to the electro-optical device, therefore represents the time that the resonator is operating in a first, modelocked pulse mode of operation.

At a time $t_1$, after a steady state modelocked pulse has developed in the resonator, periodic modulation of the applied bias voltage is discontinued and a constant (first) bias voltage is then applied to the electro-optical device, such that $R_{eff}$ is substantially 100%. In the embodiment shown in FIG. 3A, the first voltage, applied at time $t_1$, is 0 volts, meaning that the Pockels cell or other electro-optical device is completely discharged. Under this second, amplification mode of operation, the amplitude of the laser energy within the resonator is allowed to grow rapidly, drawing upon energy previously input into the lasing medium during pumping in the modelocked pulse operating mode, as described above. When the laser energy has reached a desired amplitude, it may then be released as pulsed energy having the pulse duration and energy output as described herein. This release is effected by applying a bias voltage at a later time $t_2$ such that $R_{\textit{eff}}$ is reduced to substantially 0%. According to the embodiment of FIG. 3A, the applied bias voltage at this time is substantially equal to the quarter wave voltage of the electro-optical device.

Amplification and release (or extraction) of laser energy through the application of first and second (constant) bias voltages, as described above, may also be carried out by applying bias voltages such that $R_{\textit{eff}}$ beginning at $t_1$ is less than 100%. In the amplification mode of operation, however, $R_{\textit{eff}}$ is generally greater than 80%, typically greater than about 90%, and often greater than about 95%. Likewise, laser energy may also be released at $t_2$ using an $R_{\textit{eff}}$ of greater than 0%. For example, a second bias voltage may be applied at $t_2$ such that $R_{\textit{eff}}$ is generally less than 20%, typically less than 10%, and often less than 5%. In any event, the important consideration is that the device is operated such that $R_{\textit{eff}}$ is at a relatively high value at $t_1$ and then decreased to a relatively low value at $t_2$, thereby allowing the device to amplify an oscillating laser pulse and thereafter release the amplified laser energy.

In the particular embodiment of the invention characterized by the applied bias voltage waveform shown in FIG. 3A, the voltage required to obtain an $R_{\textit{eff}}$ value of substantially 100% at $t_1$ is substantially 0 volts. The term "substantially 0 volts" indicates that the electro-optical device may be completely discharged to 0 volts or that the applied voltage will generally be less than 10%, typically less than 5%, and often less than 1%, of the quarter wave voltage of the device. Likewise, in this embodiment of the invention, the voltage required to obtain an $R_{\textit{eff}}$ value of substantially 0% is substantially equal to the quarter wave voltage. The term "substantially equal to the quarter wave voltage" indicates an applied bias voltage to the electro-optical device of its quarter wave voltage or preferably at least 80%, typically at least 90%, and often at least 95% of its quarter wave voltage.

Also, as explained previously, the Pockels cell or electro-optical device, depending on other components (e.g., a retardation plate) in the apparatus, may require voltages other than 0 and the quarter wave voltage to achieve $R_{\textit{eff}}$ values of 100% and 0%, respectively. It is also apparent from the cyclical nature of the dependency of $R_{\textit{eff}}$ on the applied bias voltage, as given by equation (1) above, that higher voltages may be applied to achieve a given effective reflectivity. For example, either 0 volts or the half wave voltage may be applied to obtain $R_{\textit{eff}}$=100% in equation (1). In general, however, it is preferred that the smallest bias voltage be applied to achieve a given $R_{\textit{eff}}$. Advantageously, the full range of effective reflectivity values, from 0% to 100%, may be obtained with the application of relatively modest bias voltages in the range from 0 volts to the quarter wave voltage, according to the methods described herein.

Figure 3B:
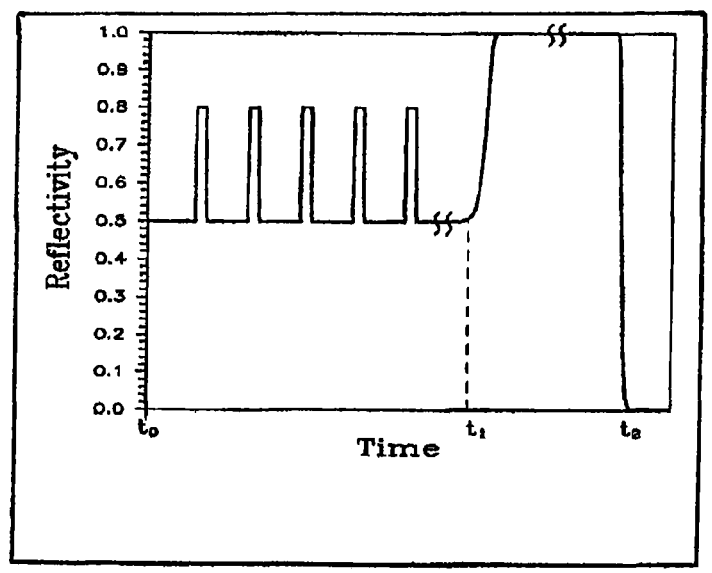
FIG. 3B is a graphical representation of the effective reflectivity over time of the combined mirror, electro-optical device, and polarizer in FIG. 2, with the time-dependent voltage applied to the electro-optical device as shown in FIG. 3A.

FIG. 3B shows, according to one embodiment of the invention, the effective reflectivity over time corresponding to the time-dependent bias voltage waveform applied to the electro-optical device, as shown in FIG. 3A. During the modelocked operating mode from $t_0$ to $t_1$, the effective reflectivity is periodically and positively offset, from a 50% operating value, to a peak value of 80%. The period of the applied voltage waveform matches that of the effective reflectivity waveform, which is the round trip time, or twice the time required for the laser energy to traverse the length of the resonator. At time $t_1$ (at the beginning of the amplification operating mode), when the electro-optical device is discharged, the corresponding value of $R_{\textit{eff}}$ is 100%. At time $t_2$, when the applied bias voltage is $V_{\lambda/4}$, $R_{\textit{eff}}$ changes to 0% to release the amplified energy.

Figure 4:
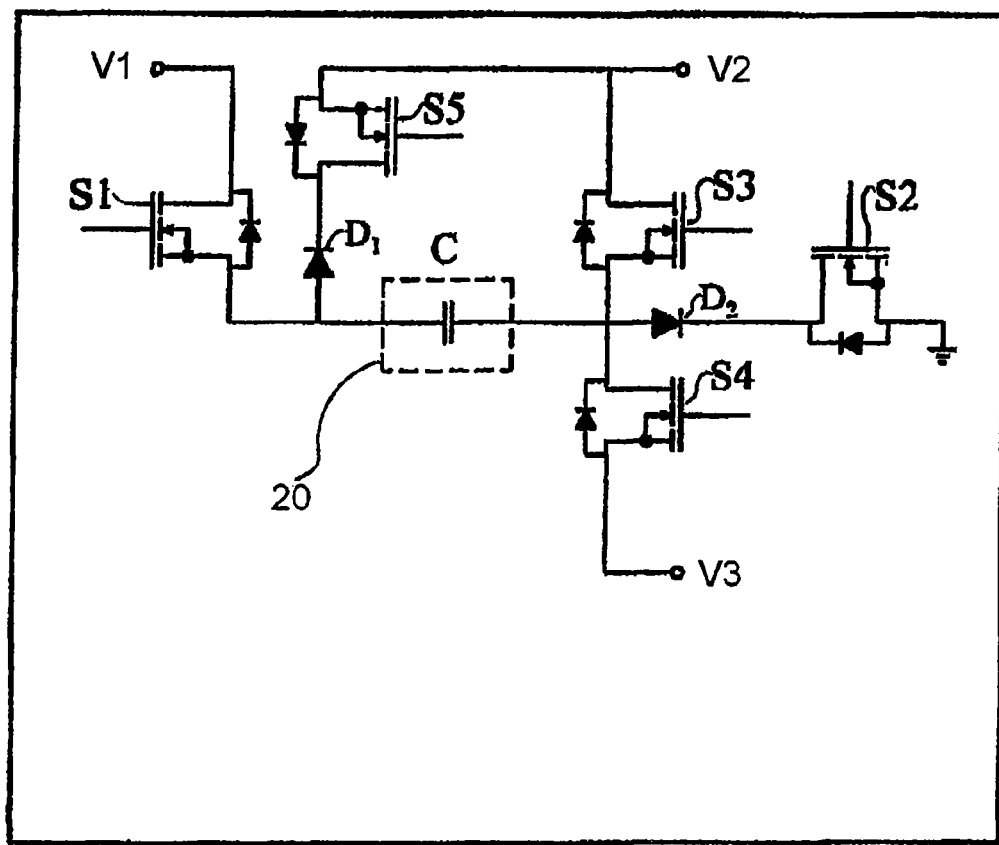
FIG. 4 is a schematic of representative waveform generating electronics, capable of delivering the time-dependent voltage to the electro-optical device, as shown in FIG. 3A.

The system for generating these waveforms represents another aspect of the present invention, as the electronics require not only a peak voltage of $V_{\lambda/4}$, but also must be capable of a modulation frequency of generally at least about 50 MHz, typically at least about 100 MHz (based on a pulse oscillation time on the order of about 10 nanoseconds), and often at least about 200 MHz. Values of the modulation frequency may therefore be within the representative ranges of from about 50 to about 200 MHz or from about 75 to about 150 MHz. In addition, the switching rise time of the modulation may be approximately 1 nanosecond. FIG. 4 depicts one possible type of waveform generating electronics for producing the bias voltage and $R_{\textit{eff}}$ waveforms shown in FIG. 3A and FIG. 3B, respectively. The configuration comprises five switches S1, S2, S3, S4, and S5, meeting the requirements set forth above. Preferably, insulated-gate, field-effect transistor (IGFET) switches are employed, such as metal oxide semiconductor field-effect transistor (MOSFET) switches. Two high speed diodes, D1 and D2, and three voltage sources V1, V2, and V3, are also included, as shown in FIG. 4.

Also included in the embodiment of FIG. 4 is a Pockels cell 20, to which the electronic components apply a time-dependent voltage waveform, such as that depicted in FIG. 3A. Electrically, the Pockels cell 20 acts as a capacitor, with a typical capacitance of about 10 picofarads (pF). As described above with respect to FIG. 3A, the waveform generating electronics in the embodiment of FIG. 4 are used for a first mode of operation at a baseline voltage $V_o$ of $0.5V_{\lambda/4}$ (or the "eighth-wave" voltage, $V_{\lambda/8}$). The baseline voltage is modulated or offset periodically by the time-dependent differential voltage $\delta V(t)$ discussed above and having a magnitude of $0.2V_{\lambda/4}$ in the particular waveform shown in FIG. 3A. In a subsequent second mode of operation, the waveform generating electronics can be used to discharge the Pockels cell (i.e., apply a constant voltage of 0 volts). Thereafter, a voltage equal to the quarter wave voltage, $V_{\lambda/4}$, of the Pockels cell 20 can be applied.

In view of FIG. 4, at time $t_0$, the initial bias voltage $V_o$ may be applied from voltage source V1 to the Pockels cell 20 by closing S1 and S2 and opening S3, S4, and S5. Under this condition, the electronic configuration shown in FIG. 4 will charge the Pockels cell to the initial bias voltage $V_o=0.5V_{\lambda/4}$. In a first, modelocked pulse mode of operation between times $t_0$ and $t_1$, S1 is maintained closed with S4 and S5 open. S2 and S3 are periodically opened and closed with the needed frequency to modulate the bias voltage (e.g., with a period substantially equal to the round trip time of laser energy in the resonator). In particular, closing S3 while opening S2 modulates the baseline voltage with the time-dependent differential voltage, $\delta V(t)$, having a magnitude of offset determined by the voltage from source V2, as shown in FIG. 4. Opening S3 while closing S2 restores the baseline voltage ($V_o=0.5V_{\lambda/4}$) from voltage source V1, through the high speed diode D2. The total bias voltage, $V(t)$, applied to the Pockels cell 20 is therefore $V_o+\delta V(t)$ during the first mode of operation.

At time $t_1$, a second, amplification mode of operation is established upon closing S3 and S5 and opening S1 and S2. This arrangement discharges the Pockels cell 20 through S3, S5, and the high speed diode D1. Finally, at time $t_2$, closing S1 and S4 while opening S2, S3, and S5 applies the quarter wave voltage, $V_{\lambda/4}$, which is the differential between voltage sources V1 and V3, to the Pockels cell 20, as needed to extract the amplified pulse. Although the Pockels cell capacitance is small, the switching currents reach several amperes as a result of the very fast switching times required. Stray capacitance and/or inductance may impact circuit performance, such that small, tight packaging is desirable.

Apparatuses and methods disclosed herein can therefore achieve a desired quality of pulsed laser energy by alternating between two modes of operation in a single resonator, rather than through the use of two separate resonators. Also, a single Pockels cell, operating in the modes discussed above, can eliminate the need for an additional modelocking device to establish a modelocked pulse within the resonator. Because the Pockels cell does not require operation at a resonant frequency, synchronization with the pulse round trip time is carried out through setting the period of the bias voltage modulation, thereby eliminating the need to adjust resonator length.

The apparatuses and methods disclosed herein are in many cases significantly simplified due to the reduced number of components and/or reduced demands in terms of bias voltage and other operating parameters. Devices may be operated using a modulated waveform according to the requirements and parameters set forth herein, and using the electronic configuration discussed above or various equivalent configurations as would be apparent to one of ordinary skill, having the benefit of the present disclosure. Other embodiments of the invention may involve the introduction of conventional optical components for use in conjunction with the apparatuses disclosed herein, such as shutters or beam attenuators, reflecting prisms or other reflecting components, filters, light focusing components such as concentrators or condensers, collimating lenses, additional polarizers, electro-optical devices, and/or mirrors, etc. These variations are readily contemplated, and the above modifications are therefore well within the purview of one or ordinary skill, having regard for the present disclosure.

In view of the above, it will be seen that several advantages may be achieved and other advantageous results may be obtained. Various changes could be made in the above apparatuses and methods without departing from the scope of the present disclosure. It is intended that all matter contained in this application, including all theoretical mechanisms and/or modes of interaction described above, shall be interpreted as illustrative only and not limiting in any way the scope of the appended claims.

Throughout this disclosure, various aspects are presented in a range format. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 5, from 3 to 6 etc., as well as individual whole and fractional numbers within that range, for example, 1, 2, 2.6, 3, 4, 5, and 6. This applies regardless of the breadth of the range.

The following example is set forth as representative of the present invention. This example is not to be construed as limiting the scope of the invention as other embodiments and aspects of the invention are apparent in view of the present disclosure.

EXAMPLE 1

A laser apparatus as described herein is used to generate pulsed laser energy having a pulse duration of about 100-200 ps with about 500-750 mj/pulse. The laser apparatus includes a resonator with two substantially totally reflective mirrors at opposite ends of its optical axis. An alexandrite crystal lasing medium, a polarizer, and a Pockels cell are positioned along this optical axis. An optical flashlamp is also included for pumping the alexandrite lasing medium, which generates laser energy having a wavelength in the range of 700-950 nm.

The pulsed laser energy described above is generated by pumping the lasing medium and first establishing a modelocked pulse oscillating in the resonator. In the modelocked pulse operating mode, a time-dependent voltage waveform, as described herein, is applied to the Pockels cell. This waveform results from the sum of a constant baseline voltage and a time-dependent differential voltage. The baseline voltage is in the range of 1000-1500 volts (representing 40%-60% of the Pockels cell quarter wave voltage, or 2500 volts) and is negatively offset or modulated by the time-dependent differential voltage, having an amplitude in the range of 250-750 volts (representing 10%-30% of the Pockels cell quarter wave voltage). The period of the resulting voltage waveform is in the range from 5-10 ns and is equal to the round trip time of the oscillating laser energy in the resonator. The voltage applied to the Pockels cell is thus modulated at a frequency in the range from 100-200 MHz.

Subsequently, the modelocked pulse established as described above is amplified by discharging the Pockels cell to essentially 0 volts. Oscillating laser energy is reflected between the mirrors at each end of the resonator, with essentially no losses. This laser energy therefore rapidly increases in amplitude by extracting energy previously pumped and stored in the alexandrite crystal during modelocking. When the laser energy has reached the desired energy level as indicated above, it is extracted from the resonator by applying the quarter wave voltage of 2500 volts to the Pockels cell.

The switching electronics used to operate the laser in modelocked pulse and amplification modes, and finally to extract the amplified pulse as discussed above, comprise five MOFSET switches, two high speed diodes, and three voltage sources having voltages V1 in the range of +1000 to +1500 volts, V2 in the range of +250 to +750 volts, and V3 in the range of −1000 to −1500 volts. The switches, diodes, and voltage sources are configured as shown in FIG. 4.

Laser energy having the pulse duration and energy as described above is applied to a patient undergoing treatment for the removal of a tattoo. This laser energy is applied over the course of a 30-minute treatment session to all areas of the skin having undesired tattoo pigment particles. Photomechanical disruption of these particles is effected using the short pulse duration (below the transit time of a sound wave through the targeted tattoo pigment particles), together with a fluence in the range of 2-4 j/cm$^2$. This fluence is achieved with a laser energy spot diameter of about 5 mm.

Most if not all of the undesired tattoo pigment particles are effectively photomechanically disrupted, destabilized, and/or broken apart using one or two treatments. As a result, the disrupted particles are cleared from the body via normal physiological processes, such as the immune response. The tattoo is thus eventually cleared from the skin with no remaining visible signs. In this manner, various methods described herein are considered methods for treating or removing pigmented particles such as tattoo particles.

What is claimed is:

1. A method for treating a skin pigmentation comprising pigment particles using a photomechanical process, the method comprising exposing at least one pigment particle to pulsed laser energy generated using Nd:YAG, titanium doped sapphire (TIS) crystal, or alexandrite as a lasing medium and with pulses having a duration that is a multiple of the acoustic transit time across said pigment particle to photomechanically disrupt the pigment particle.

2. The method of claim 1 wherein said pulses have an energy of at least 100 mj.

3. The method of claim 1 wherein said duration is less than 1 nanosecond.

4. The method of claim 1 wherein said duration is at most 500 ps.

5. The method of claim 1 wherein said pulses have a duration of between 100 ps and 300 ps.

6. The method of claim 1 wherein said pulses have a duration of between 100 ps and 500 ps.

7. The method of claim 1 wherein the duration is below twice the acoustic transit time across said pigment particle.

8. The method of claim 1 wherein the duration is below five times the acoustic transit time across said pigment particle.

9. The method of claim 1 wherein the duration is from two times to five times the acoustic transit time across the pigment particle.

10. The method of claim 1 wherein the pigment particle is in one of a tattoo, a birthmark, or a pigment particle in a pigmented lesion.

11. The method of claim 1 wherein the at least one pigment particle has a diameter of from 1 micron to 10 microns.

12. The method of claim 1 wherein pulsed laser energy is generated using Nd:YAG as a lasing medium.

13. The method of claim 1 wherein pulsed laser energy is generated using titanium doped sapphire (TIS) crystal as a lasing medium.

14. The method of claim 1 wherein pulsed laser energy is generated using alexandrite as a lasing medium.

* * * * *